(12) United States Patent
Chang et al.

(10) Patent No.: US 9,853,611 B2
(45) Date of Patent: Dec. 26, 2017

(54) INSTRUMENTATION AMPLIFIER WITH DIGITALLY PROGRAMMABLE INPUT CAPACITANCE CANCELLATION

(71) Applicant: Northeastern University, Boston, MA (US)

(72) Inventors: Chun-hsiang Chang, Natick, MA (US); Marvin Onabajo, Jamaica Plain, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/114,447

(22) PCT Filed: Mar. 2, 2015

(86) PCT No.: PCT/US2015/018231
§ 371 (c)(1),
(2) Date: Jul. 27, 2016

(87) PCT Pub. No.: WO2015/131172
PCT Pub. Date: Sep. 3, 2015

(65) Prior Publication Data
US 2016/0344352 A1 Nov. 24, 2016

Related U.S. Application Data

(60) Provisional application No. 61/946,022, filed on Feb. 28, 2014.

(51) Int. Cl.
*H03F 3/45* (2006.01)
*H03F 1/34* (2006.01)
(Continued)

(52) U.S. Cl.
CPC ............ *H03F 1/34* (2013.01); *A61B 5/0402* (2013.01); *A61B 5/0476* (2013.01);
(Continued)

(58) Field of Classification Search
CPC .................................... H03F 1/14; H03F 3/45
(Continued)

(56) References Cited

U.S. PATENT DOCUMENTS 5,392,784 A * 2/1995 Gudaitis .............. A61B 5/0428
128/902
5,625,361 A 4/1997 Garrity et al.
(Continued)

OTHER PUBLICATIONS

R. F. Yazicioglu, et al., "A 60 μW 60 nV/√Hz Readout Front-End for Portable Biopotential Acquisition Systems," IEEE Journal of Solid-State Circuits, May 2007, vol. 42, No. 5, pp. 1100-1110.
(Continued)

*Primary Examiner* — Steven J Mottola
(74) *Attorney, Agent, or Firm* — Posternak Blankstein & Lund LLP

(57) ABSTRACT

An instrumentation amplifier that includes input capacitance cancellation is provided. The architecture includes programmable capacitors between the input stage and a current feedback loop of the instrumentation amplifier to cancel input capacitances from electrode cables and a printed circuit board at the front end. An on-chip calibration unit can be employed to calibrate the programmable capacitors and improve the input impedance.

16 Claims, 21 Drawing Sheets

(51) Int. Cl.
*A61B 5/0402* (2006.01)
*A61B 5/0476* (2006.01)

(52) U.S. Cl.
CPC ..... *H03F 3/45183* (2013.01); *H03F 3/45197* (2013.01); *H03F 3/45475* (2013.01); *H03F 2200/261* (2013.01); *H03F 2200/408* (2013.01); *H03F 2203/45048* (2013.01); *H03F 2203/45288* (2013.01); *H03F 2203/45528* (2013.01); *H03F 2203/45674* (2013.01); *H03F 2203/45682* (2013.01); *H03F 2203/45694* (2013.01)

(58) Field of Classification Search
USPC .................................................. 330/260, 292
See application file for complete search history.

(56) References Cited

U.S. PATENT DOCUMENTS

| 7,863,980 B2 | 1/2011 | Golden et al. |
| 2003/0073916 A1 | 4/2003 | Yonce |
| 2004/0158167 A1 | 12/2004 | Smith et al. |
| 2006/0015033 A1 | 1/2006 | Blakley et al. |
| 2008/0204126 A1 | 8/2008 | Wang et al. |
| 2012/0176523 A1 | 7/2012 | Yoo |
| 2014/0266482 A1 | 9/2014 | Ishii |

OTHER PUBLICATIONS

N. Verma, et al., "A Micro-Power EEG Acquisition SoC With Integrated Feature Extraction Processor for a Chronic Seizure Detection System," IEEE Journal of Solid-State Circuits, Apr. 2010, vol. 45, No. 4, pp. 804-816.
J. Xu, et al., "A 160μW 8-Channel Active Electrode System for EEG Monitoring," in IEEE International Solid-State circuits Conference (ISSCC) Digest of Technical Papers, Feb. 22, 2011, pp. 300-302.
A. Casson, et al., "Wearable Electroencephalography," IEEE Engineering in Medicine and Biology Magazine, May/Jun. 2010, vol. 29, No. 3, pp. 44-56.
Y. M. Chi, et al., "Dry-Contact and Noncontact Biopotential Electrodes: Methodological Review," IEEE Reviews in Biomedical Engineering, Oct. 2010, vol. 3, No. 1, pp. 106-119.
C. Assambo, et al., "Amplifier Input Impedance in Dry Electrode ECG Recording," in Proc. Annual IEEE Conf. Engineering in Medicine and Biology Society (EMBS), Sep. 2-6, 2009, pp. 1774-1777.
K. Soundararajan, et al., "Nonideal Negative Resistors and Capacitors Using an Operational Amplifier," IEEE Transactions on Circuits and Systems, Sep. 1975, vol. 22, No. 9, pp. 760-763.
R. Martins, et al., "A CMOS IC for Portable EEG Acquisition Systems," IEEE Instrumentation and Measurement Technology Conference, St. Paul, Minnesota, USA, May 18-21, 1998, pp. 1406-1410.
A. Worapishet, et al., "A CMOS Instrumentation Amplifier With 90-dB CMRR at 2-MHz Using Capacitive Neutralization: Analysis, Design Considerations, and Implementation," IEEE Transactions on Circuits and Systems-I: Regular Papers, Apr. 2011, vol. 58, No. 4, pp. 699-710.
Analog Devices, Precision Instrumentation Amplifier—AD8221. Online: http://www.analog.com/static/imported-files/data_sheets/AD8221.pdf, (2011).
Q. Fan, et al., "A 1.8 μW 60nV/√Hz Capacitively-Coupled Chopper Instrumentation Amplifier in 65 nm CMOS for Wireless Sensor Nodes," IEEE Journal of Solid-State Circuits, Jul. 2011, vol. 46, No. 7, pp. 1534-1543.
A. I. Larky, "Negative-Impedance Converters," IRE Transactions on Circuit Theory, Sep. 1957, vol. 4, No. 3, pp. 124-131.
Y. Li, et al., "Analog Integrated Circuits Design for Processing Physiological Signals," IEEE Reviews in Biomedical Engineering, 2010, vol. 3, pp. 93-105.
A. Arnaud, et al., "Nanowatt, Sub-nS OTAs, With Sub-10-mV Input Offset, Using Series-Parallel Current Mirrors," IEEE Journal of Solid-State Circuits, Sep. 2006, vol. 41, No. 9, pp. 2009-2018.
B. Linares-Barranco, et al., "On the Design and Characterization of Femtoampere Current-Mode Circuits," IEEE Journal of Solid-State Circuits, Aug. 2003, vol. 38, No. 8, pp. 1353-1363.
Y. Ni, et al., "A low-power temperature-compensated CMOS relaxation oscillator," Analog Integrated Circuits and Signal Processing, May 2014, vol. 79, No. 2, pp. 309-317.
L. Xu, et al., "Test Signal Generation for the Calibration of Analog Front-End Circuits in Biopotential Measurement Applications," in Proc. IEEE Intl. Midwest Symp. on Circuits and Systems (MWSCAS), Aug. 2014, pp. 949-952.
K. Wang, et al., "A Fully-Differential CMOS Low-Pass Notch Filter for Biosignal Measurement Devices with High Interference Rejection," in Proc. IEEE Intl. Midwest Symp. on Circuits and Systems (MWSCAS), Aug. 2014, pp. 1041-1044.

\* cited by examiner

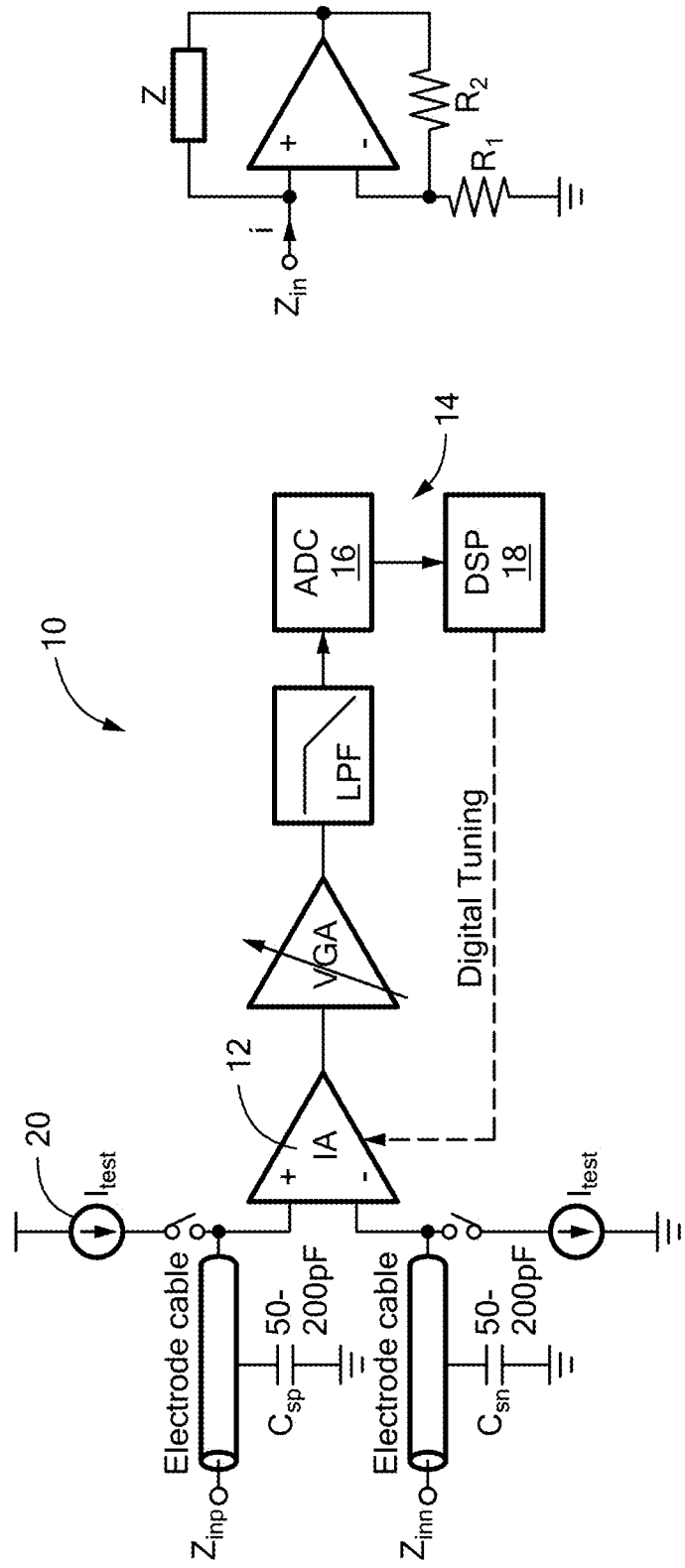

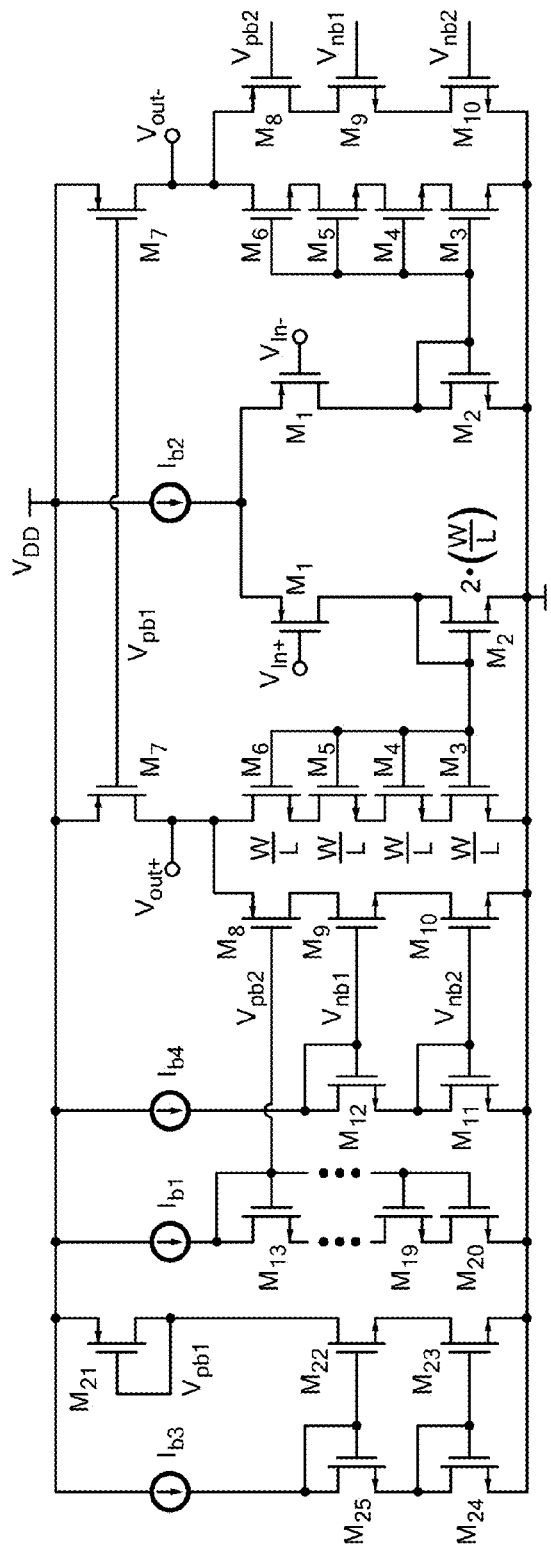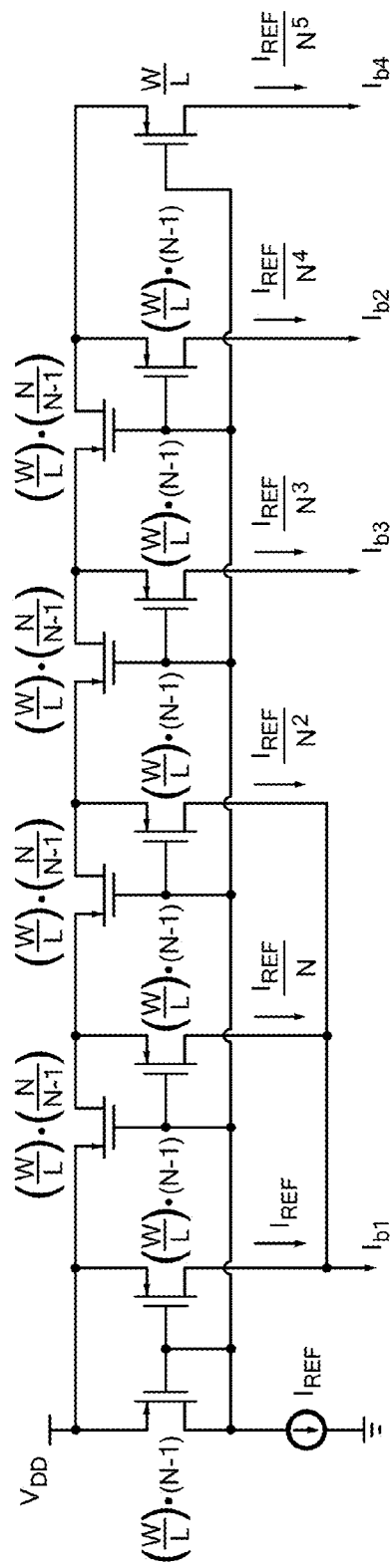
*FIG. 11(a)*   *FIG. 11(b)*

INSTRUMENTATION AMPLIFIER WITH DIGITALLY PROGRAMMABLE INPUT CAPACITANCE CANCELLATION

CROSS-REFERENCE TO RELATED APPLICATIONS

This application claims the benefit under 35 U.S.C. §119(e) of U.S. Provisional Patent Application No. 61/946,022, filed Feb. 28, 2014, entitled Instrumentation Amplifier With Built-In Digitally Programmable Input Capacitance Cancellation, the disclosure of which is incorporated by reference herein in its entirety.

STATEMENT REGARDING FEDERALLY SPONSORED RESEARCH OR DEVELOPMENT

This invention was made with government support under grant No. 1349692 awarded by NSF. The government has certain rights in the invention.

BACKGROUND

Battery-powered portable or implantable biopotential and bioimpedance measurement devices are becoming increasingly widespread in the medical diagnostics field. The signal acquisitions of the main biosignal-sensing applications such as electroencephalography (EEG) and electrocardiography (ECG) involve voltage measurements from a few microvolts to several millivolts [1]-[3]. Biopotentials are conventionally acquired using electrodes covered with electrolyte gels or solutions to decrease the contact impedance at the skin interface to values below 10 KΩ. However, wet-contact measurements cause discomfort and dry out in novel long-term monitoring applications such as in brain-computer interfaces where EEG signals are acquired and analyzed over hours or longer [4].

In general, dry electrodes such as inexpensive Ag/AgCl are better suited for long-term monitoring, but their use is associated with increased contact resistances that can be above 1 MΩ [5]. This characteristic complicates the measurement of small biopotentials in the range of few μV for EEG applications by requiring very high input impedance at the analog front-end amplifier of at least 500 MΩ [6]. Nevertheless, a significant problem is that this impedance is affected by parasitic capacitances of the integrated circuit package as well as electrode cable and printed circuit board (PCB) capacitances that could be as high as 50-200 pF at the input of an instrumentation amplifier (IA) shown in FIG. 1. For instance, when the goal is to record EEG signals with frequencies up to 100 Hz, an interface capacitance of 200 pF would limit the input impedance at 100 Hz to approximately 8 MΩ, which is much less than 500 MΩ and would cause excessive attenuation such that the EEG signal cannot be measured reliably.

SUMMARY OF THE INVENTION

An instrumentation amplifier (IA) with a mechanism that generates negative capacitances at its input is provided to enable input capacitance cancellation for biosignal measurements, such as biopotential and bioimpedance. In one embodiment, the IA architecture includes two digitally programmable (8-bit) capacitors between the input stage and the current feedback loop of the IA to cancel the input capacitances from electrode cables and a printed circuit board. The negative capacitance generation technique can improve the input impedance from a few mega ohms to more than 100 MΩ without significant impact on performance parameters such as the common-mode rejection ratio (CMRR), power supply rejection ratio (PSRR), total harmonic distortion (THD), and noise.

In another aspect, an on-chip digital calibration system is provided to adaptively improve the input impedance of the analog front-ends in biosignal measurement systems. The calibration system can be activated, for example, whenever electrode cables are changed. In one embodiment, the calibration unit controls the two 8-bit capacitor banks of the IA to generate a negative capacitance and to significantly increase the input impedance of the IA to above at least 100 MΩ. A test signal generator for operation with the calibration system is also provided to calibrate the IA. The integrated signal generator enables detection of the input impedance at the front-end IA based on current injection and amplitude detection.

In one embodiment, an instrumentation amplifier device is provided comprising an instrumentation amplifier comprising:
 a differential input stage comprising an inverting input terminal and a non-inverting input terminal;
 an output stage driven by the input stage;
 a direct current feedback loop from the output stage to the input stage; and
 a negative capacitance generation feedback circuit between the input stage and the direct current feedback loop, wherein a negative capacitance is generated at the input stage to cancel parasitic capacitances at the input terminal and thereby boost input impedance.

In one aspect of the instrumentation amplifier device, the negative capacitance generation feedback circuit is connected in parallel between the input stage and internal nodes of the instrumentation amplifier. In a further aspect, gains from the internal nodes are out of phase.

In a further aspect, the negative capacitance generation feedback circuit comprises a first negative impedance converter circuit connected in parallel between the inverting input terminal and a first internal node; and a second negative impedance converter connected in parallel between the non-inverting terminal and an second internal node.

In a further aspect, each negative impedance converter circuit comprises a plurality of programmable capacitors disposed in parallel. In a still further aspect, each programmable capacitor is disposed in series with a switch operable between an on position and an off position. In a still further aspect, each programmable capacitor comprises an 8-bit device comprising 8 capacitors, each capacitor selectable to be on or off. In a still further aspect, the instrumentation amplifier is calibratable by setting each programmable capacitor to be on or off to maximize the input impedance boosting.

In a further aspect, a gain from the first internal node is out of phase with a gain from the second internal node. In a still further aspect, the gain from the first internal node is 180° out of phase with the gain from the second internal node.

In one aspect of the instrumentation amplifier device, the negative capacitance generation feedback circuit cancels at least in part input capacitance to the input stage generated by one or more of an electrode cable, a printed circuit board, and an integrated circuit package connected to the input stage.

In one aspect of the instrumentation amplifier device, the negative capacitance generation feedback circuit is operable to boost the input impedance to at least 100 MΩ.

In one aspect of the instrumentation amplifier device, the instrumentation amplifier is operable to sense biopotential signals.

In one aspect, the instrumentation amplifier is operable to sense voltages representative of electroencephalography or electrocardiography biosignals.

In one aspect, the instrumentation amplifier device is operable to measure input biosignals having frequencies of up to at least 50 Hz.

In one aspect of the instrumentation amplifier device, the instrumentation amplifier includes programmable capacitors to generate the negative capacitance at the input of the instrumentation amplifier, and further comprises a calibration circuit comprising a processor operative in a calibration mode to:

measure voltage at an output node of the instrumentation amplifier or of a subsequent gain or filtering stage;

compare the measured voltage amplitude to a plurality of reference voltages;

generate a respective plurality of control signals responsive to the comparison; and transmit the generated control signals to control the programmable capacitors of the instrumentation amplifier to optimize the negative capacitance generated at the input of the instrumentation amplifier.

In one aspect, the calibration circuit includes an analog-to-digital converter operative to provide the reference voltages.

In a further aspect, the calibration circuit further includes a calibration unit comprising input ports to receive input signals from the analog to digital converter and a plurality of output ports to transmit control signals to switches at the programmable capacitors.

In one aspect, the calibration unit further comprises memory to store a code representative of a control signal to optimize the negative capacitance.

In one aspect, the calibration circuit includes a test current generator operative to inject a test current having a selected magnitude into the input of the instrumentation amplifier to generate a voltage at the output node.

In one aspect, the calibration circuit includes one or more switches in a calibration path operative when closed to allow activation of the calibration device.

In one embodiment, a biosignal sensing device comprises the instrumentation amplifier, the biosignal sensing device operable to sense voltages representative of electroencephalography or electrocardiography biosignals.

In one embodiment, a method of measuring biosignals comprises:

receiving biosignals at an input stage of an instrumentation amplifier, the input stage including an inverting input terminal and a non-inverting input terminal;

generating an amplified output signal at an output stage of the instrumentation amplifier;

generating within the instrumentation amplifier a feedback loop from the output stage to the input stage; and boosting impedance at the input stage by generating a negative capacitance in the feedback loop.

In one aspect, the method includes generating the negative capacitance by providing negative impedance converter circuitry connected in parallel between the input stage and internal nodes of the instrumentation amplifier.

In one aspect of the method, the internal nodes have out-of-phase gains.

In one aspect of the method, the method includes connecting electrode cables to the input stage of the instrumentation amplifier; and calibrating the negative capacitance converter circuitry after connecting the electrode cables to maximize the boosting of the impedance at the input stage.

In one aspect of the method, the negative capacitance converter circuitry comprises a plurality of programmable capacitors, and the calibrating step comprises setting each of the programmable capacitors to on or off.

In one aspect of the method, the method includes receiving voltages representative of electroencephalography or electrocardiography signals.

In one aspect of the method, the method includes connecting electrode cables to each of the inverting input terminal and the non-inverting input terminal, the electrode cables connected to electrodes.

In one aspect of the method, the electrodes comprise dry electrodes.

In one aspect of the method, the method includes boosting the impedance to at least 100 MΩ.

In one embodiment, a method of generating negative capacitances via on-chip calibration, comprises:

measuring, by a processor, voltage at an output node of an instrumentation amplifier or of subsequent gain/filtering stages, the instrumentation amplifier including programmable capacitors to generate a negative capacitance at an input of the instrumentation amplifier;

comparing, by the processor, the measured voltage amplitude to a plurality of reference voltages;

generating, by the processor, a respective plurality of control signals responsive to the comparison; and transmitting, by the processor, the generated control signals to control the programmable capacitors of the instrumentation amplifier to optimize the negative capacitance generated at the input of the instrumentation amplifier.

In one aspect, the method includes storing a code in memory representative of a control signal to optimize the negative capacitance.

In one aspect of the method, the method includes cycling through a plurality of comparison voltages and updating the code stored in the memory with an optimized code.

In one aspect of the method, the method includes injecting a test current having a selected magnitude into the input of the instrumentation amplifier to generate the voltage at the output node.

DESCRIPTION OF THE DRAWINGS

The invention will be more fully understood from the following detailed description taken in conjunction with the accompanying drawings in which:

FIG. 1 is a schematic illustration of an embodiment of an analog front-end system for biosignal measurements including an instrumentation amplifier with on-chip input capacitance cancellation and calibration;

FIG. 2 is an illustration of a basic negative impedance converter (NIC) as reference, where $Z_{in}=-Z$ when $R_1=R_2$;

FIG. 11(a) illustrates an operational transconductance amplifier for use during the test current injection at the input of an embodiment of an instrumentation amplifier;

FIG. 11(b) illustrates a bias current generation circuit for use in the operational transconductance amplifier of FIG. 11(a);

DETAILED DESCRIPTION OF THE INVENTION

Referring to FIG. 1, an instrumentation amplifier device 10 is shown that incorporates an instrumentation amplifier (IA) 12 with negative capacitance generation feedback (NCGFB) and associated calibration circuit 14. In one embodiment, the negative capacitance generation is integrated into the IA, described further below. In addition, on-chip monitoring and calibration can be provided using an analog to digital converter (ADC) 16 and a digital signal processor (DSP) 18 with a programmable capacitor bank within the IA 12 for tuning The calibration circuit also includes an on-chip test current generator ($i_{test}$) 20 with high output impedance. The instrumentation amplifier is suitable, for example, in an analog front-end of, for example, a bio-signal sensing device.

In one embodiment, a solution for boosting input impedance is the addition of a classical negative impedance converter (NIC) at the input of the IA. FIG. 2 shows a simplified NIC schematic that could be used to generate a negative capacitance at the input node of the IA if Z is a capacitor. However, this approach would require an additional amplifier, whose power and area consumption is undesirable. Furthermore, the additional noise from the operational amplifier at the input of the IA would have to be carefully assessed.

Accordingly, a negative capacitance generation scheme is provided that is integrated into the IA and thereby avoids an extra amplifier. The IA with input capacitance cancellation for impedance boosting has general usefulness in emerging biopotential and bioimpedance measurement applications regardless of how the tuning method is implemented.

Figure 3:
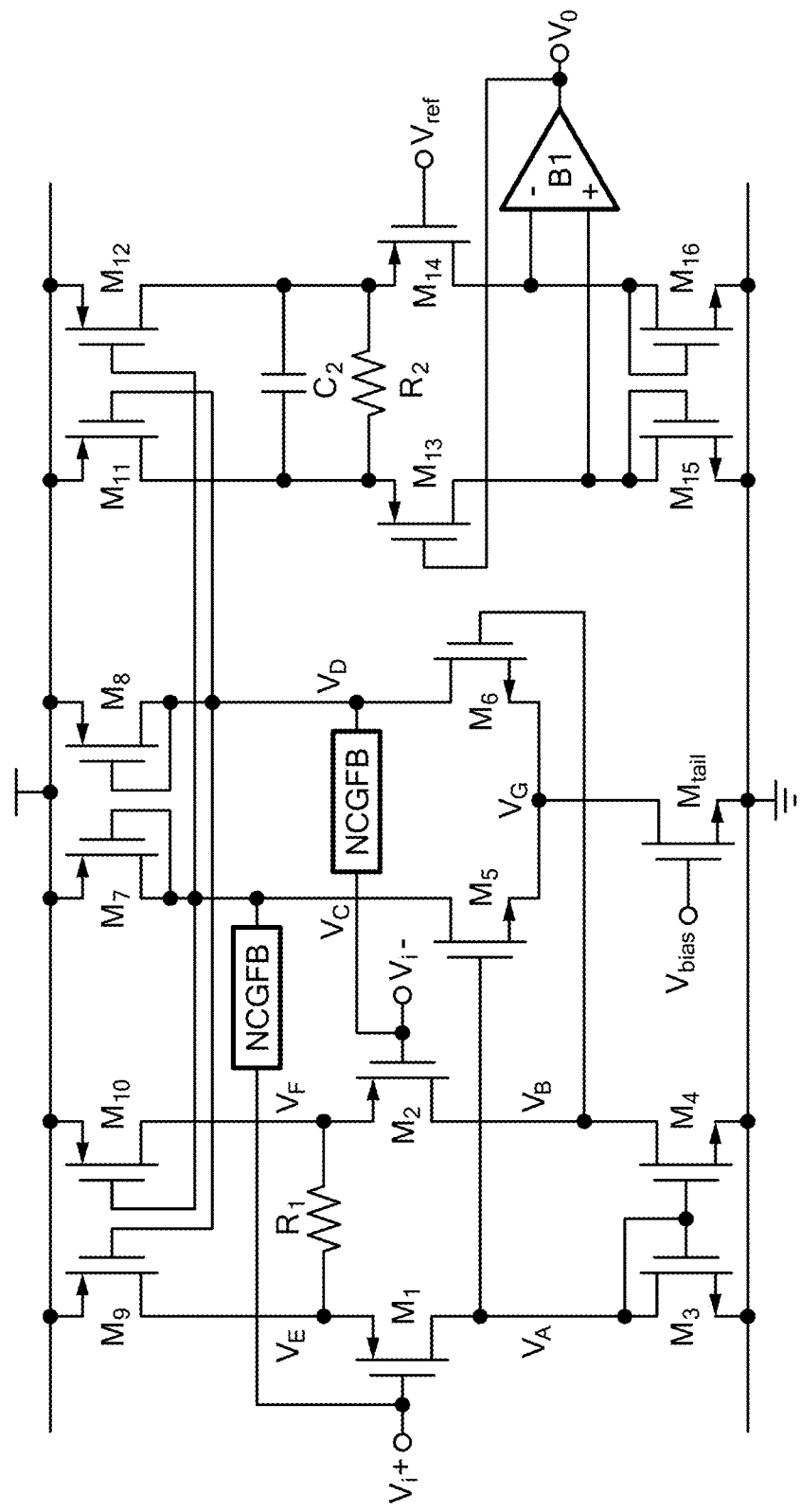
FIG. 3 is a schematic diagram of an instrumentation amplifier with direct current feedback and negative capacitance generation feedback (NCGFB)

Referring again to FIG. 1, an instrumentation amplifier device 10 includes an instrumentation amplifier 12 that includes a differential input stage comprising an inverting input terminal and a non-inverting input terminal, and an output stage driven by the input stage. A direct current feedback loop is provided from the output stage to the input stage (FIG. 3, described further below). A negative capacitance generation feedback circuit is disposed between the input stage and the direct current feedback loop, such that a negative capacitance is generated at the input stage to cancel parasitic capacitances at the input terminal and thereby boost input impedance. The negative capacitance can be implemented by, for example, a plurality of programmable capacitors (described further below). Digital tuning can be implemented via a calibration circuit including the ADC 16 to provide reference voltages to a calibration unit (DSP 18) that includes input ports to receive input signals from the ADC and a plurality of output ports to transmit control signals to switches at the programmable capacitors in the IA 12. The DSP also includes memory to store codes representative of control signals to optimize the negative capacitance. The calibration circuit 14 also includes a test current generator 20 that can inject a test current having a selected magnitude into the input of the instrumentation amplifier to generate a voltage at the output node, used in the calibration process. The calibration circuit also includes one or more switches in a calibration path operative when closed to allow activation of the calibration circuit. Calibration can be performed at any appropriate time (prior to measurements), such as when the electrode cables are changed.

One embodiment of an IA with input capacitance cancellation for impedance boosting is described more particularly with reference to FIG. 3. FIG. 3 shows a schematic of a suitable IA topology with direct current feedback, where the DC gain of the IA is decided by the ratio $R_2/R_1$ and the dominant pole depends on $R_2$ and $C_2$. The amplifier B1 can be implemented in any suitable manner, as would be known by one of ordinary skill in the art. The IA includes a differential input stage comprising an inverting input terminal and a non-inverting input terminal, and an output stage driven by the input stage. A direct current feedback loop is provided from the output stage to the input stage. A negative capacitance generation feedback (NCGFB) circuit is provided between the input stage and the direct current feedback loop. With the NCGFB circuit, negative capacitances are generated at the input stage to cancel parasitic capacitances at the input terminal and thereby boost input impedance.

More particularly, the negative capacitance generation feedback circuit is connected in parallel between the input stage and internal nodes of the instrumentation amplifier. In one embodiment, the negative capacitance generation feedback circuit comprises a first negative impedance converter circuit connected in parallel between the inverting input terminal and a first internal node; and a second negative impedance converter connected in parallel between the non-inverting terminal and a second internal node. The internal nodes are preferably selected such that their gains are out of phase, preferably 180° out of phase.

Figure 4:
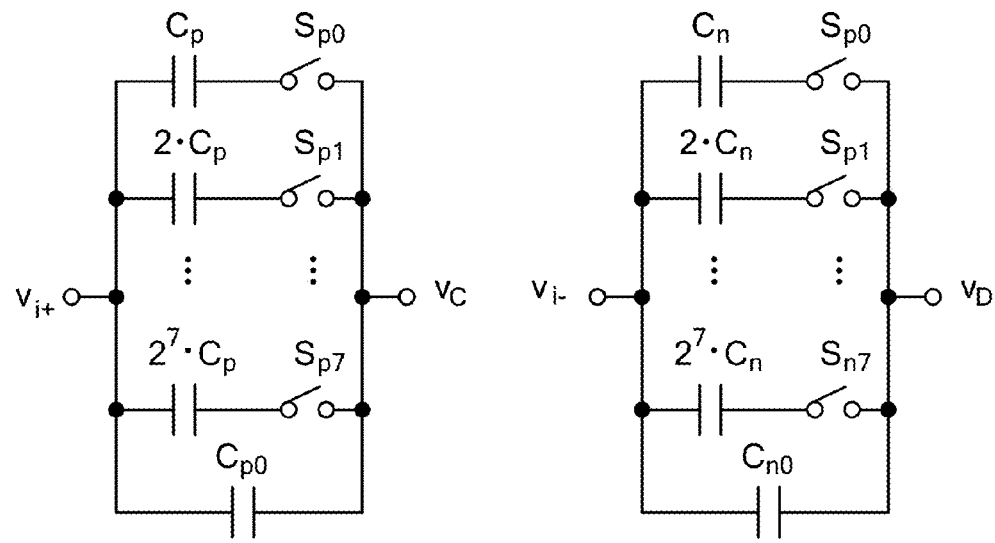
FIG. 4 illustrates an implementation of negative capacitance generation feedback with programmable capacitors.

In one embodiment, each negative impedance converter circuit comprises a plurality of programmable capacitors $C_p$, $C_n$, disposed in parallel, indicated in FIG. 4. Each programmable capacitor is disposed in series with a $S_p$, $S_n$, switch operable between an on position and an off position. In one embodiment, each programmable capacitor comprises an 8-bit device comprising 8 capacitors. As described further below, the instrumentation amplifier can be calibrated by setting each programmable capacitor to be on or off to maximize the input impedance boosting. The calibration can be performed whenever appropriate, such as when the input electrode cables are changed.

The negative capacitance generation feedback circuit can be operable to and can be calibrated to boost the input impedance to at least 100 MΩ, at least 200 MΩ, at least 300 MΩ, at least 400 MΩ, at least 500 MΩ, at least 750 MΩ, at least 1000 MΩ, at least 1500 MΩ, at least 2000 MΩ, depending on the requirements of the particular application for which the IA is used. The IA can be operable to measure input biosignals having frequencies of up to 50 Hz, up to 100 Hz, up to 200 Hz, up to 300 Hz, up to 400 Hz, up to 500 Hz, up to 600 Hz, up to 700 Hz, up to 800 Hz, up to 900 Hz, or up to 1000 Hz, again depending on the requirements of the particular application for which the IA is used and the chip fabrication process technology in which the IA is manufactured. In some applications, the IA can be incorporated into a biosignal sensing device to sense voltages representative of electroencephalography or electrocardiography signals.

The transfer functions from the inputs ($v_{i+}$, $v_{i-}$) to $v_A$, $v_B$, $v_C$, $v_D$, $v_E$, and $v_F$ are analyzed below using a small-signal model to evaluate the possibilities for negative capacitance generation feedback (NCGFB). Since nodes $v_C$ and $v_D$ in FIG. 3 are the most appropriate locations to obtain suitable gains for generating negative capacitances at the inputs ($v_{i+}$, $v_{i-}$), the NCGFB realization at these two nodes is discussed further below.

Figure 5:
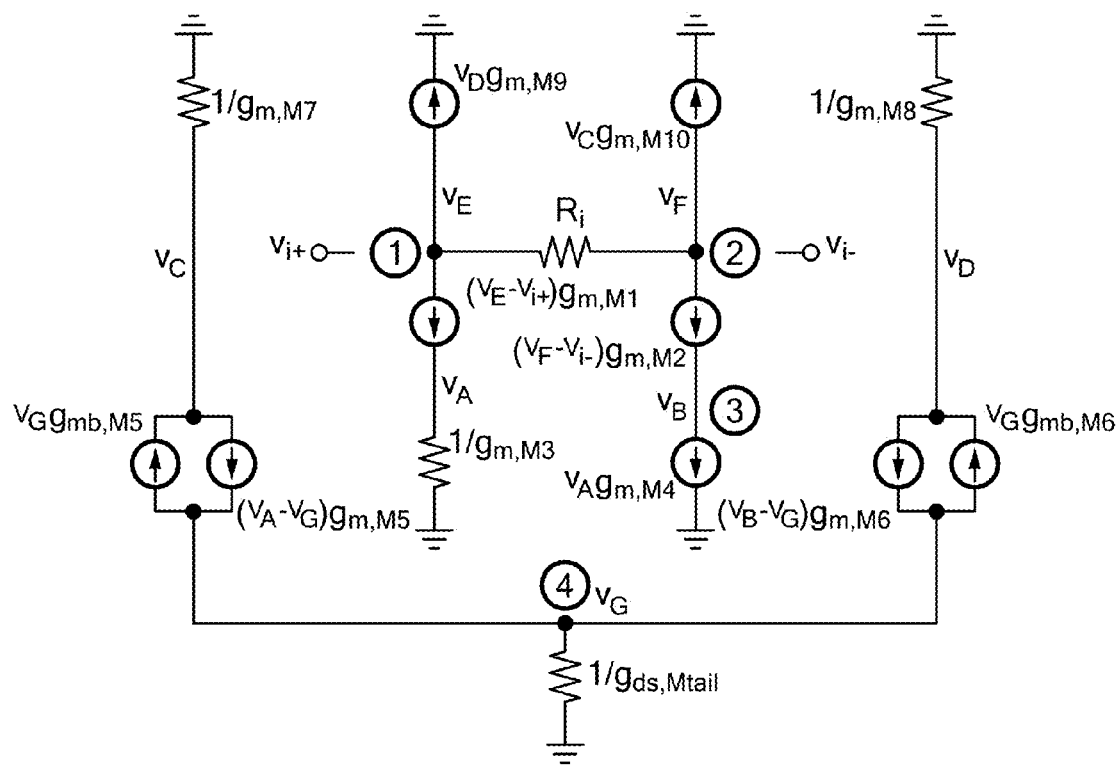
FIG. 5 illustrates a small-signal model of the instrumentation amplifier's input and feedback stages.

FIG. 5 shows the small-signal model of the IA's input stage and the current feedback loop for solving the transfer functions from the inputs to internal nodes. All parasitic capacitances are omitted during this analysis because the typical applications of this IA are at low frequencies (below 1 KHz). It is also noteworthy that the small-signal inputs ($v_A$ and $v_B$) of the differential pair ($M_5$ and $M_6$) in the feedback loop are not truly differential due to the asymmetric characteristics looking into $v_A$ ($M_3$ is diode-connected) and $v_B$ ($M_4$ is not diode-connected). Hence, the phase of $v_B$ follows that of $v_A$, and $v_G$ is not a virtual ground. For this reason, the small-signal drain-source resistance ($1/g_{ds,Mtail}$) of $M_{tail}$ should be taken into account during the analysis. Without the effect of the NCGFB, the current summation equations at nodes 1 through 4 in FIG. 5 are:

$$\frac{v_E - v_F}{R_1} + g_{m,M1}(v_E - v_{i+}) + g_{m,M9}v_D = 0, \quad (1)$$

$$\frac{v_E - v_F}{R_1} + g_{m,M2}(v_F - v_{i-}) - g_{m,M10}v_C = 0, \quad (2)$$

$$g_{m,M2}(v_F - v_{i-}) - g_{m,M4}v_A = 0, \quad (3)$$

$$(g_{m,M5} + g_{mb,M5} + g_{m,M6} + g_{mb,M6} + g_{ds,Mtail})v_G - \quad (4)$$
$$g_{m,M5}v_A - g_{m,M6}v_B = 0;$$

where $g_{m,M1}$-$g_{m,M10}$ are the transconductances of $M_1$-$M_{10}$, $g_{mb,M5}$ and $g_{mb,M6}$ are the body effect transconductances of $M_5$ and $M_6$, and $g_{ds,Mtail}$ is the small-signal drain-source admittance of $M_{tail}$. From FIG. 5, the voltages $v_A$, $v_C$, and $v_D$ can be expressed as $$v_A = \frac{g_{m,M1}(v_E - v_{i+})}{g_{m,M3}}, \quad (5)$$

$$v_C = \frac{(g_{m,M5} + g_{mb,M5})v_G - g_{m,M5}v_A}{g_{m,M7}}, \quad (6)$$

$$v_D = \frac{(g_{m,M6} + g_{mb,M6})v_G - g_{m,M6}v_A}{g_{m,M8}}. \quad (7)$$

Note that the conditions $g_{m1}=g_{m2}$, $g_{m3}=g_{m4}$, $g_{m5}=g_{m6}$, $g_{m7}=g_{m8}$, $g_{m9}=g_{m10}$, and $g_{mb5}=g_{mb6}$ are valid for this analysis in the absence of device mismatches. Furthermore, the same definitions as in [8] are used next: $v_{in}=v_{i+}-v_{i-}=v_E-v_F$, where $v_{i+}=v_{in}/2$ and $v_{i-}=-v_{in}/2$. With these definitions, the voltage gains from $v_{in}$ to $v_{A-G}$ can be derived from the above equations:

$$A_{V,A} = \frac{v_A}{v_{in}} = \frac{g_{m,M7} \cdot g_{ds,Mtail}}{D}, \quad (8)$$

$$A_{V,B} = \frac{v_B}{v_{in}} = \frac{2g_{m,M7}}{g_{m,M5} \cdot g_{m,M9} \cdot R_1} + \frac{g_{m,M7} \cdot g_{ds,Mtail}}{D}, \quad (9)$$

$$A_{V,C} = \frac{v_C}{v_{in}} = \frac{1}{g_{m,M9} \cdot R_1} - \frac{g_{m,M3} \cdot g_{m,M7} \cdot g_{ds,Mtail}}{g_{m,M9} \cdot D}, \quad (10)$$

$$A_{V,D} = \frac{v_D}{v_{in}} = -\frac{1}{g_{m,M9} \cdot R_1} - \frac{g_{m,M3} \cdot g_{m,M7} \cdot g_{ds,Mtail}}{g_{m,M9} \cdot D}, \quad (11)$$

$$A_{V,E} = \frac{v_E}{v_{in}} = \frac{1}{2} + \frac{g_{m,M3} \cdot g_{m,M7} \cdot g_{ds,Mtail}}{g_{m,M1} \cdot D}, \quad (12)$$

$$A_{V,F} = \frac{v_F}{v_{in}} = -\frac{1}{2} + \frac{g_{m,M3} \cdot g_{m,M7} \cdot g_{ds,Mtail}}{g_{m,M1} \cdot D}, \quad (13)$$

$$A_{V,G} = \frac{v_G}{v_{in}} = \frac{2 \cdot g_{m,M3} \cdot g_{m,M7}^2}{g_{m,M9} \cdot D}; \quad (14)$$

where:
$D=[(2 \cdot g_{m,M5}+2 \cdot g_{mb,M5}+g_{ds,Mtail}) \cdot g_{m,M3} \cdot g_{m,M7}-g_{m,M5} \cdot g_{m,M9} \cdot g_{ds,Mtail}] \cdot R_1$. From Equations (8) and (9) it can be observed that $A_{V,B}$ is always larger than $A_{V,A}$, and that $A_{V,A}$ and $A_{V,B}$ have the same phase. Equations (10) and (11) show that $A_{V,C}$ and $A_{V,D}$ are in anti-phase. Although these gain magnitudes are not equal, nodes $v_C$ and $v_D$ are well-suited as points at which the NCGFB can be added. From Equations (12) and (13), the gains $A_{V,E}$ and $A_{V,F}$ have the same phase if $g_{m,M3} \cdot g_{m,M7} \cdot g_{ds,Mtail}/(g_{m,M1} \cdot D)>0.5$, which would complicate the use of nodes $v_E$ and $v_F$ for the NCGFB.

Returning to FIG. 4, a suitable NCGFB implementation is illustrated with an 8-bit digitally-controlled capacitor ($C_p$-$2^7 \cdot C_p$) and one fixed capacitor ($C_{p0}$) between nodes $v_{i+}$ and $v_C$. The maximum and minimum capacitance values occur with $S_{p7,6,5,4,3,2,1,0}$=[11111111] and [00000000] respectively, where '1' or '0' indicate that the switch is turned "on" or "off". The same programmable capacitor configuration was connected between nodes $v_{i-}$ and $v_D$ with control switches $S_{n7,6,5,4,3,2,1,0}$. Neglecting the very high resistance at the gates of the transistors, the input impedances ($Z_{inp}$ and $Z_{inn}$) in FIG. 1 can be derived as $$Z_{inp}(s) = \frac{1}{sC_{sp} + sC_{total,i+}}, \quad (15)$$

$$Z_{inn}(s) = \frac{1}{sC_{sn} + sC_{total,i-}}; \quad (16)$$

where $C_{sp}$ and $C_{sn}$ are the cable (and PCB) capacitances at the positive and negative inputs of the IA, and $C_{total,i+}$ and $C_{total,i-}$ represent the IA's total equivalent capacitances at the input $v_{i+}$ and $v_{i-}$ respectively. The tuning range of the 8-bit capacitors can be designed to compensate for the 50-200 pF capacitances from the cables and PCB by generating negative $C_{total,i+}$ and $C_{total,i-}$ values through the presented NCGFB configuration. This property becomes evident after using Miller approximations to express $C_{total,i+}$ and $C_{total,i-}$ in terms of previously derived gains:

$$C_{total,i+} = C_{gs,M1}(1 - 2A_{V,E}) + \quad (17)$$
$$C_{gd,M1}(1 - 2A_{V,A}) + \left[C_{p0} + C_p \cdot \sum_{i=0}^{7} (2^i \cdot S_{pi})\right] \cdot (1 - 2A_{V,C}),$$

$$C_{total,i-} = C_{gs,M2}(1 + 2A_{V,F}) + \quad (18)$$
$$C_{gd,M2}(1 + 2A_{V,B}) + \left[C_{n0} + C_n \cdot \sum_{i=0}^{7} (2^i \cdot S_{ni})\right] \cdot (1 + 2A_{V,D});$$

where $C_{gs,X}$ and $C_{gd,X}$ are the parasitic gate-source and gate-drain capacitances of transistor $M_X$.

Simulation Results

A 93.6 μW IA, using the circuitry in FIG. 3, was designed in IBM 0.13-μm CMOS technology for EEG signal measurement applications. A commensurate IA without NCGFB was designed as reference for comparison. Table 1 contains the design parameters of both IAs. Identical supply voltages of 1.2 V and total currents of 78 μA were used for both designs. $C_{p0}$, $C_p$, $C_{n0}$ and $C_n$ were selected to cover cable/PCB capacitances from 50 pF to 200 pF for the IA across all device corner model cases. Notice that $C_{p0}$ is not equal to $C_{n0}$, and that $C_p$ is not equal to $C_n$ due to the different gains and phases, as discussed above. Implementing large capacitors as off-chip capacitors is frequently done in analog front-ends for biosignal acquisitions. Therefore, it is assumed here that $C_2$ would not be laid out on the chip.

Table 2 summarizes the simulated specification parameters of both IAs. The two designs have the same gain, bandwidth, output offset voltage and noise in the typical corner case with $C_{sp}$=$C_{sn}$=200 pF (FIG. 1). The common-mode rejection ratio (CMRR) was designed to be comparable to a commercial IA. The results show that there are only minor differences (0.1 to 0.2 dB) in the common mode rejection ratio (CMRR), power supply rejection ratio (PSRR), and total harmonic distortion (THD) of both IAs.

TABLE 1

PARAMETERS OF THE IA DESIGNS WITHOUT AND WITH NCGFB

| Component/Parameter | Without NCGFB | With NCGFB |
|---|---|---|
| $V_{DD}$ [V] | 1.2 | 1.2 |
| Power supply current [μA] | 78 | 78 |
| $R_1$ [KΩ] | 0.7 | 0.7 |
| $R_2$ [KΩ] | 40 | 40 |
| $C_2$ [nF] | 41.2 | 41.2 |
| $C_{p0}$ [pF] | — | 4.3 |
| $C_p$ [pF] | — | 0.082 |
| $C_{n0}$ [pF] | — | 2.32 |
| $C_n$ [pF] | — | 0.028 |

TABLE 2

COMPARISON OF SIMULATION RESULTS

| Performance | Without NCGFB | With NCGFB |
|---|---|---|
| Gain [dB] | 32.2 | 32.2 |
| Bandwidth [Hz] | 100 | 100 |
| CMRR @10 Hz [dB]* | 87.4 | 87.1 |
| PSRR @10 Hz [dB]* | 67.2 | 66.9 |
| THD @10 Hz [dB]* for 1 $mV_{pk-pk}$ input | −51.2 | −51.1 |
| Output offset voltage [mV]* | 1.8 | 1.8 |
| Total input-referred volatage noise [μV] (noise bandwidth: 0.1-100 Hz) | 2.72 | 2.72 |

*Results are the mean from 500 Monte Carlo simulation runs including process and mismatch variations from foundry-supplied device models.

Figure 6A:
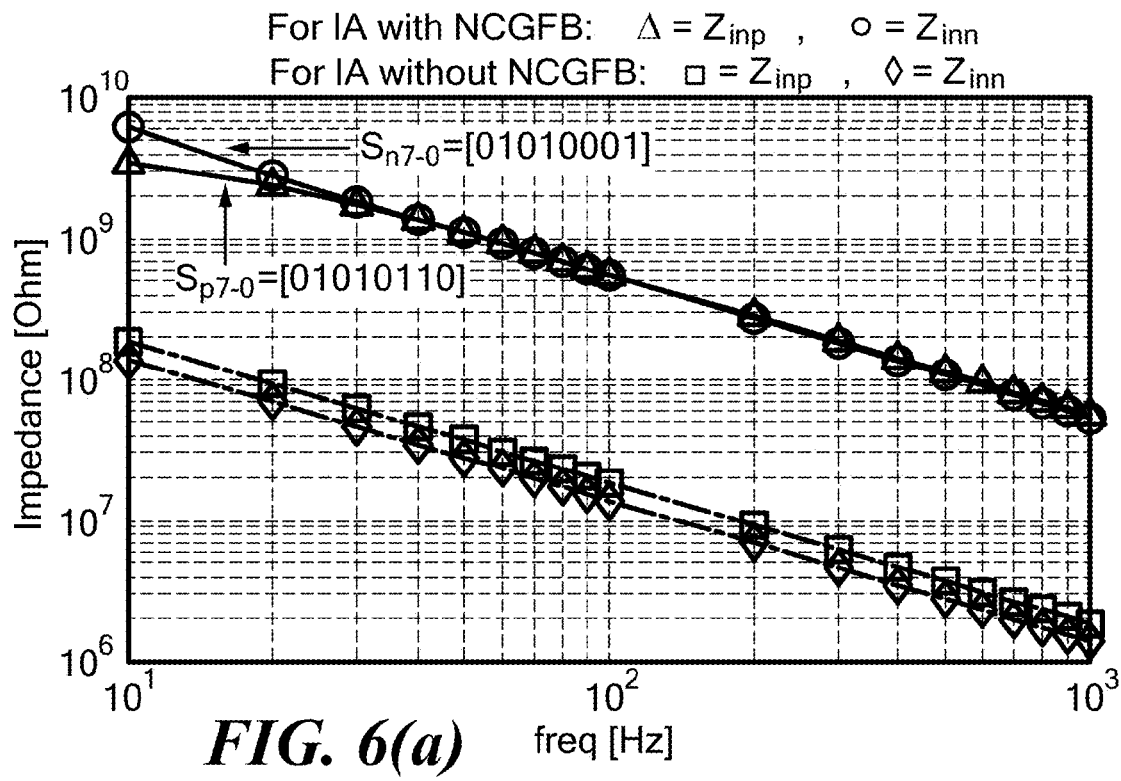
FIG. 6 illustrates impedances at the instrumentation amplifier inputs with and without NCGFB for different $C_{sp}$ and $C_{sn}$ values: (a) $C_{sp}=C_{sn}=100$ pF, (b) $C_{sp}=200$ pF and $C_{sn}=50$ pF.
Figure 6B:
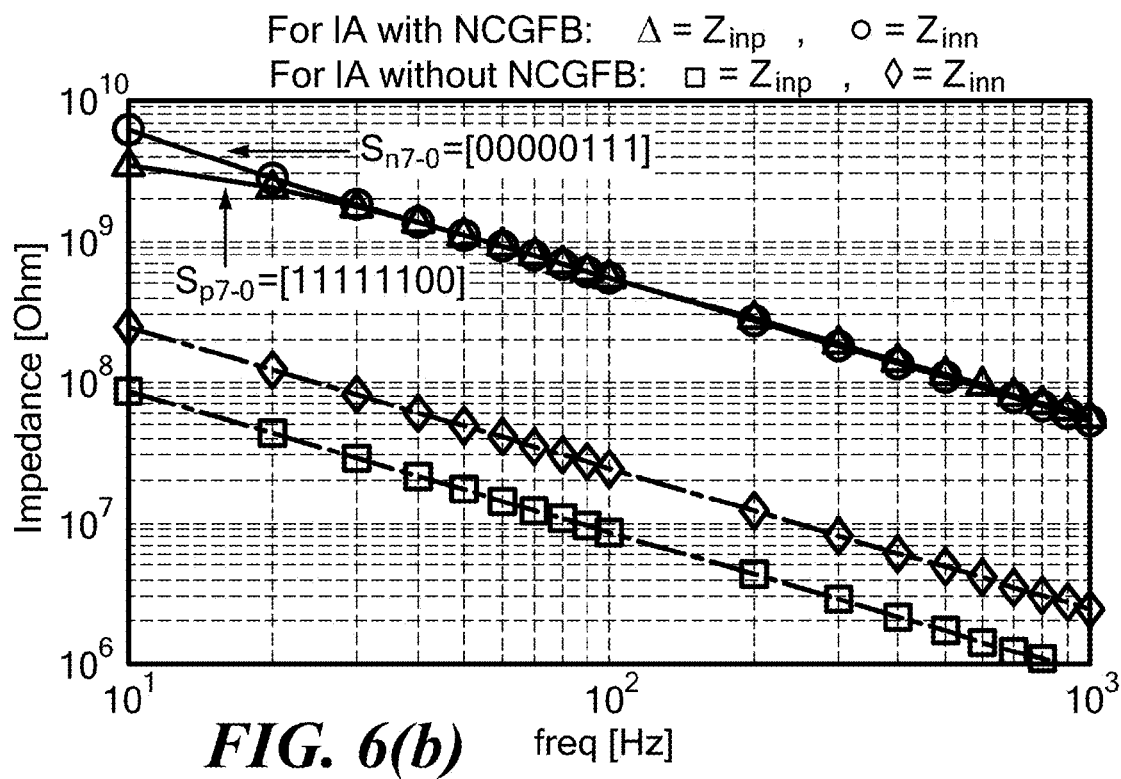

FIG. 6 shows the input impedances of $Z_{inp}$ and $Z_{inn}$ for both amplifiers in the typical corner case for different $C_{sp}$ and $C_{sn}$ values. The impedances at $Z_{inp}$ and $Z_{inn}$ for the IA with NCGFB reach 500 MΩ or more at 100 Hz. A tuning scheme, discussed further below, is used to adjust the programmable capacitors in FIG. 4 to a value that cancels most of the capacitance at each input. For example, the case with $C_{sp}$=$C_{sn}$=100 pF in FIG. 6(a) requires that $S_{p7,6,5,4,3,2,1,0}$=[01010110] and $S_{n7,6,5,4,3,2,1,0}$=[01010001]. On the other hand, without the NCGFB method, the impedances at $Z_{inp}$ and $Z_{inn}$ are only below 20 MΩ at 100 Hz, which fall short of the 500 MΩ requirement for measurements with dry electrodes. The simulation results in FIG. 6(b) indicate that the IA with NCGFB has the capability to compensate for different cable capacitances at each input ($c_{sp}$=200 pF and $c_{sn}$=50 pF).

Figure 7:
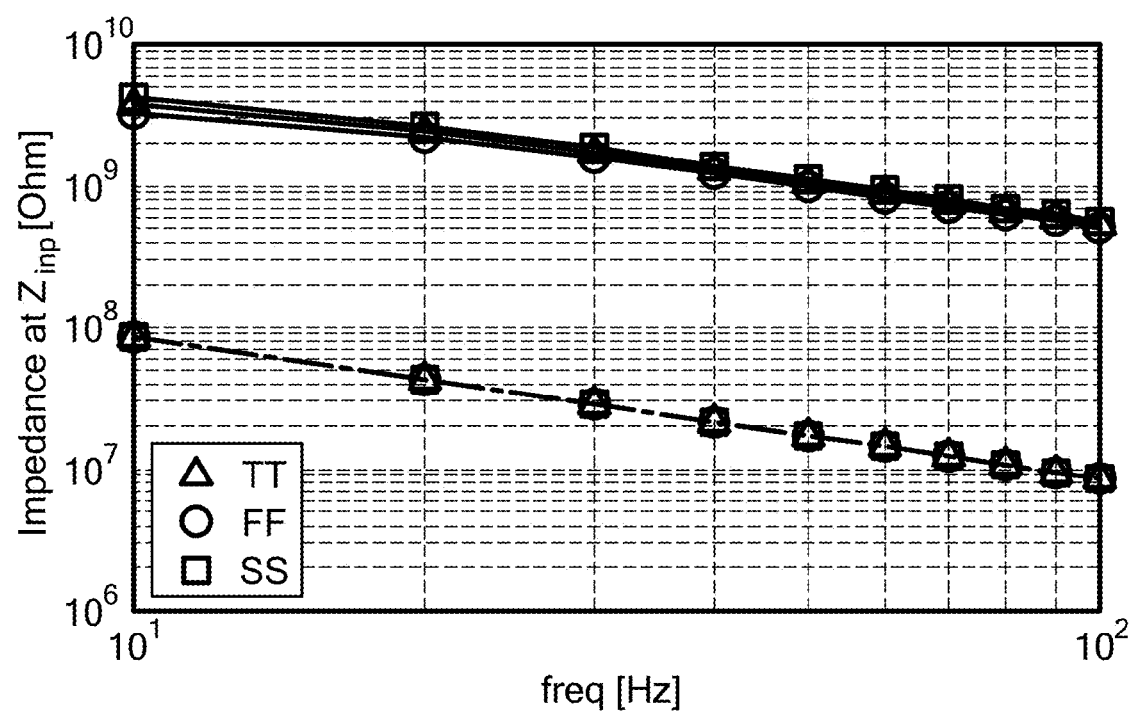
FIG. 7 an illustrates input impedance comparison (at $Z_{inp}$) for the instrumentation amplifiers with and without NCGFB from simulations with foundry-supplied device models representing different process corner cases.

FIG. 7 shows the impedances at $Z_{inp}$ for the IAs with and without NCGFB in the different process corner cases with $C_{sp}$=200 pF. The impedances at 100 Hz for the IA with NCGFB are over 500 MΩ in all corner cases after adjusting the switch settings ($S_{p7,6,5,4,3,2,1,0}$) of the capacitor array. In contrast, the impedances at 100 Hz for the IA without NCGFB are less than 20 MΩ in all process corner cases.

In summary, a 93.6 μW IA with negative capacitance generation was presented in IBM 0.13-μm CMOS technology to cancel input capacitances from the electrode cables and PCB. In comparison to an identical IA without NCGFB, the important performances such as common-mode rejection ratio (CMRR), power supply rejection ratio (PSRR), and total harmonic distortion (THD) are not significantly affected by the proposed input capacitance cancellation technique. The IA with NCGFB does not consume any extra power to boost the impedance from below 20 MΩ to above 500 MΩ after the proper adjustment of the digitally programmable capacitors.

Figure 8:
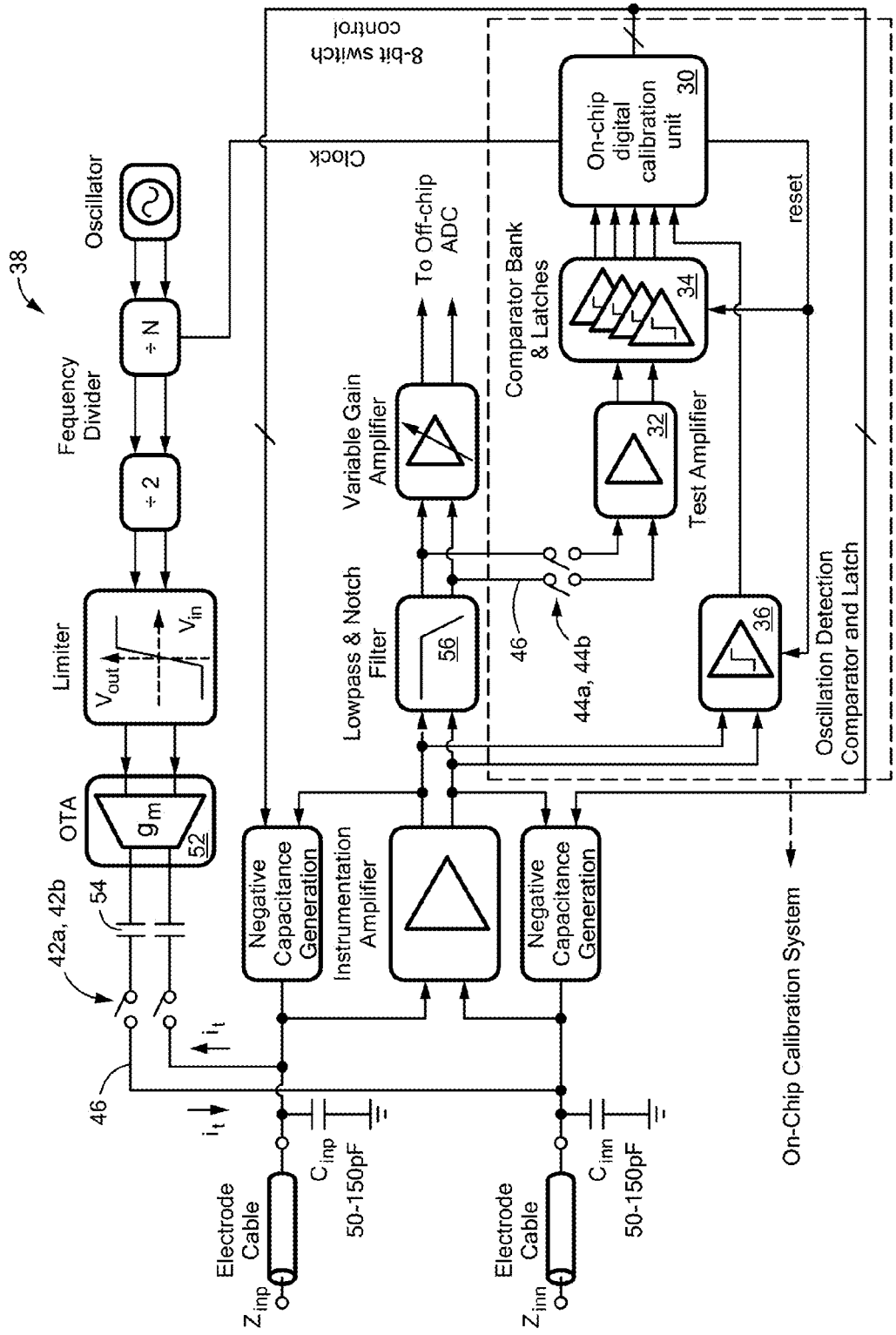
FIG. 8 is a schematic illustration of one embodiment of an instrumentation amplifier in the analog front-end with on-chip calibration circuitry.

As noted above, an on-chip digital calibration circuit 14 is provided to automatically boost the input impedance of the instrumentation amplifier (IA) in analog front-ends for electroencephalography (EEG) measurements with dry electrodes. FIG. 8 schematically illustrates one embodiment of an EEG measurement front-end developed as a single-chip implementation.

The input impedance is affected by parasitic capacitances from the package of the integrated circuit as well as electrode cable and printed circuit board (PCB) capacitances that can be 50-150 pF at the IA input, which are modeled as $C_{inp}$ and $C_{inn}$ in FIG. 8. The IA described above utilizes a negative capacitance generation technique to boost the input impedance from a few megaohms to above 500 MΩ.

Referring to FIG. 8, one embodiment of the calibration system includes of a digital calibration unit 30, a test amplifier 32, a set of four comparators 34 to detect the amplitude as described further below, and one comparator 36 to detect if an oscillation occurs. The calibration unit automatically finds the optimum code for the two capacitor banks between the input stage and the current feedback loop of the IA to cancel the unwanted input capacitances. The calibration test currents are generated by the test signal generation circuitry 38 described further below. When the four switches 42*a*, 42*b*, 44*a*, 44*b*, in FIG. 8 are closed, the system operates in calibration mode such that a test signal current, for example, a 19.5 Hz test signal current, ($i_t$) is injected into the circuit under test and the calibration system is connected to the signal path 46. DC decoupling capacitors 54 are inserted at output of an operational transconductance amplifier (OTA) 52 to prevent leakage currents. The power line interference is suppressed by the notch in the low-pass filter response 56. The calibration technique takes advantage of the knowledge that the filter output amplitude reflects the equivalent impedance at the instrumentation amplifier input because the test current magnitude is known. The minimum acceptable output amplitude can be determined based on simulations with worst-case process-voltage-temperature variations prior to selecting the number of comparators and their reference voltage levels. NOR-type SR latches are connected at the output of the comparators to hold the outputs until the reset signal.

Figure 9:
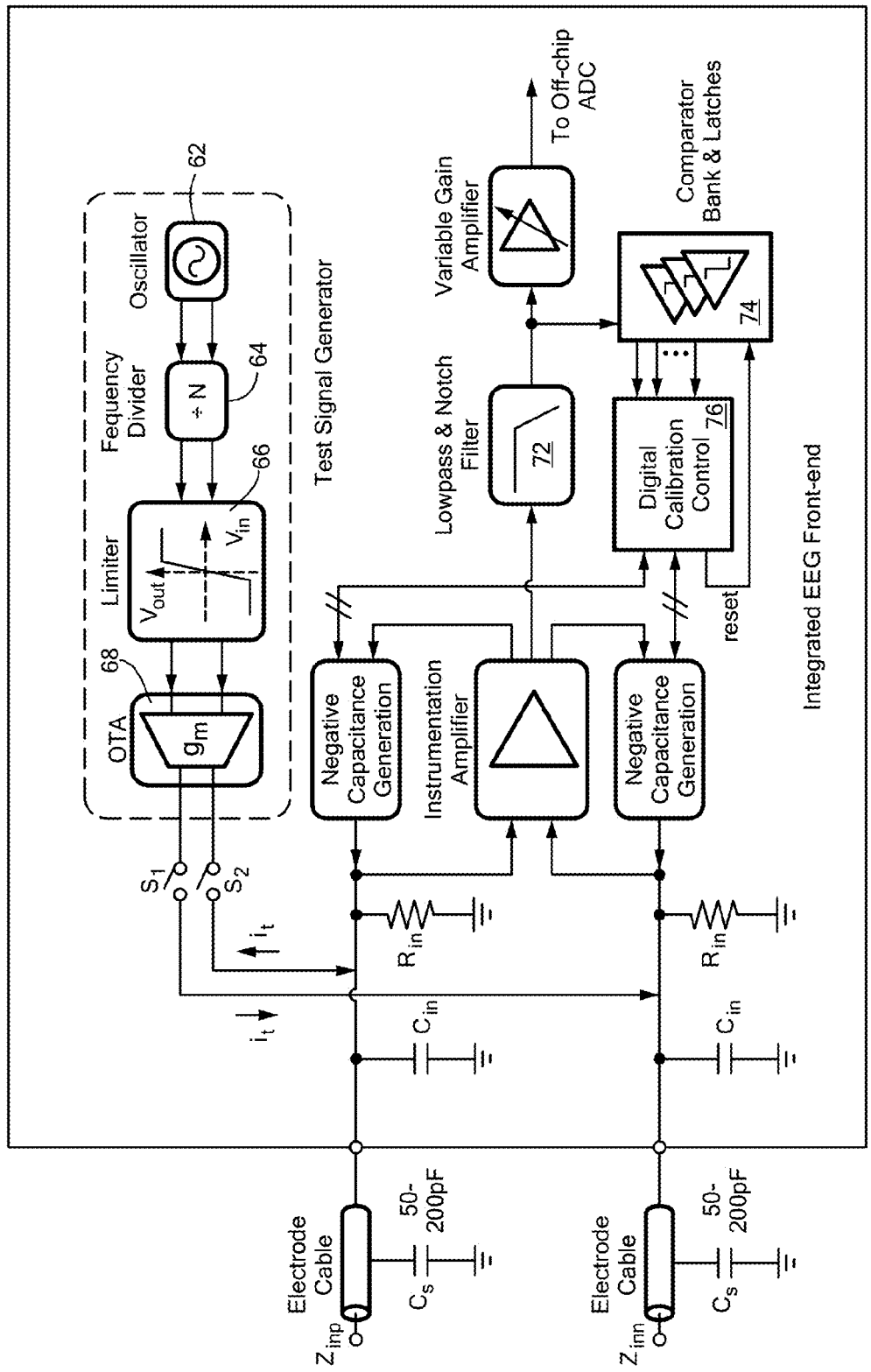
FIG. 9 is a schematic illustration of one embodiment of an instrumentation amplifier with on-chip test signal generation for calibration of the instrumentation amplifier.

One embodiment of a test signal generator for use in the calibration system is described with reference to FIGS. 9-19. As depicted in the embodiment of FIG. 9, the test signal generator includes a relaxation oscillator 62, a frequency divider 64, a voltage limiter 66, and a low-transconductance OTA 68. The on-chip oscillator generates a 20 KHz rail-to-rail square wave, which is divided down to 19.5 Hz. The voltage limiter converts the rail-to-rail signal to a level that is compatible with the OTA input requirement.

A first calibration step is performed with open electrodes in FIG. 9, where the switches $S_1$ and $S_2$ are closed to inject differential test currents ($i_t$) from an operational transconductance amplifier (OTA) into both input nodes to generate a voltage swing. The calibration step is repeated until the negative capacitance value is adjusted for sufficient input capacitance cancellation to meet the high input impedance requirement. In each cycle, the output of the lowpass and notch filter (LPF) is monitored as visualized in FIG. 10, taking advantage of the fact that the output amplitude (with combined amplifier and low pass filter (LPF) 72 gain of around 100 in this design) reflects the equivalent impedance at the instrumentation amplifier input because the test current magnitude is known. The amplitude of the signal can be determined based on simulations with worst-case process-voltage-temperature variations prior to selecting the number of comparators and their reference voltage levels. In one embodiment, a comparator bank 74 having a plurality of comparators is used to identify the amplitude around the required peak voltage swing (with minimum acceptable input impedance). Any suitable number of comparators can be used; generally one comparator can be suitable in some applications (when the manufacturing process variations are small), but 4 comparators are used in the embodiment shown for enhanced resolution and robust operation during the amplitude detection. In each cycle, the latched outputs of the comparators can be interpreted as thermometer-coded representation of the front-end input impedance. Prior to the reset in every cycle, the digital calibration control block 76 saves and compares the current code with the previous codes. The negative capacitance value is adjusted step by step by cycling through all digital settings to identify the one that results in the maximum output voltage swing that corresponds to the maximum front-end input impedance condition. This approach avoids direct measurement of the input impedance by using low-power area-efficient circuits in an amplitude detection scheme. Even though only one comparator would be needed in the typical case to check if the LPF output amplitude is large enough for a given input impedance requirement, a bank of comparators can be used to ensure detection capability in the presence of process variations, which can be evaluated with statistical simulations. If three or more sequential settings result in the same maximum amplitude code, then the negative capacitance setting in the center can be selected.

FIG. 11(*a*) shows an embodiment of a suitable OTA and FIG. 11(*b*) shows its biasing circuit. The OTA should have significantly higher output impedance than the impedance of the node into which the current is injected. As an example, if the input impedance requirement of the instrumentation amplifier (IA) is 500 MΩ, an OTA output impedance of at least 1 GΩ up to 100 Hz is targeted to avoid excessive loading effects. Moreover, the maximum output capacitance target for the OTA design is 200 fF to ensure that it is small compared to the total capacitance ($C_{in}$ in FIG. 9) after partial capacitance cancellation. Due to the high impedance at the IA input, a differential test current magnitude of 1 pA was chosen to keep the input voltage swing at the injection node in the millivolts range, which maintains linear operation of the IA and LPF. This requires an OTA with very small transconductance around 25 pS (with $V_{in}=V_{in+}-V_{in-}=40$ mV$_{peak}$).

In one example, the instrumentation amplifier can have a simulated input-referred noise of 2.5 μV in the band of the interest (0.01 Hz to 100 Hz), and the OTA can generate 78 μV output-referred noise integrated from 0.01 Hz to 100 Hz. Hence, the total noise is small compared to the approximately 4 mV peak-to-peak differential swing at the instrumentation amplifier inputs (see FIG. 12). To obtain the result in this figure, the test current generator was simulated with 3 pF capacitances at the OTA output nodes, which ensures that the front-end input impedance is higher than 500 MΩ in the 100 Hz band of interest (i.e., after partial input capacitance cancellation).

Figure 10:
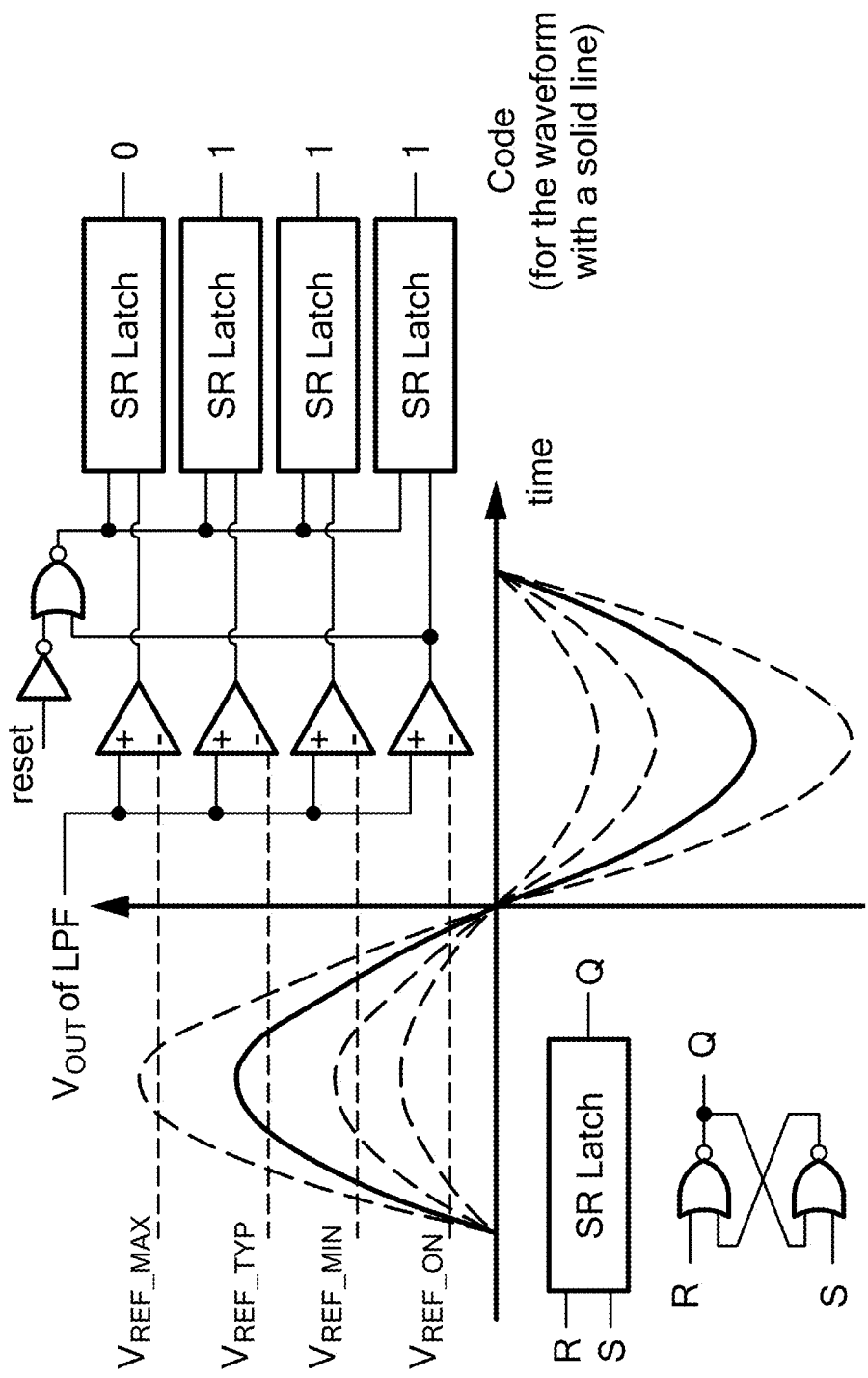
FIG. 10 illustrates an amplitude-based impedance detection method with comparators and latches.
Figure 12:
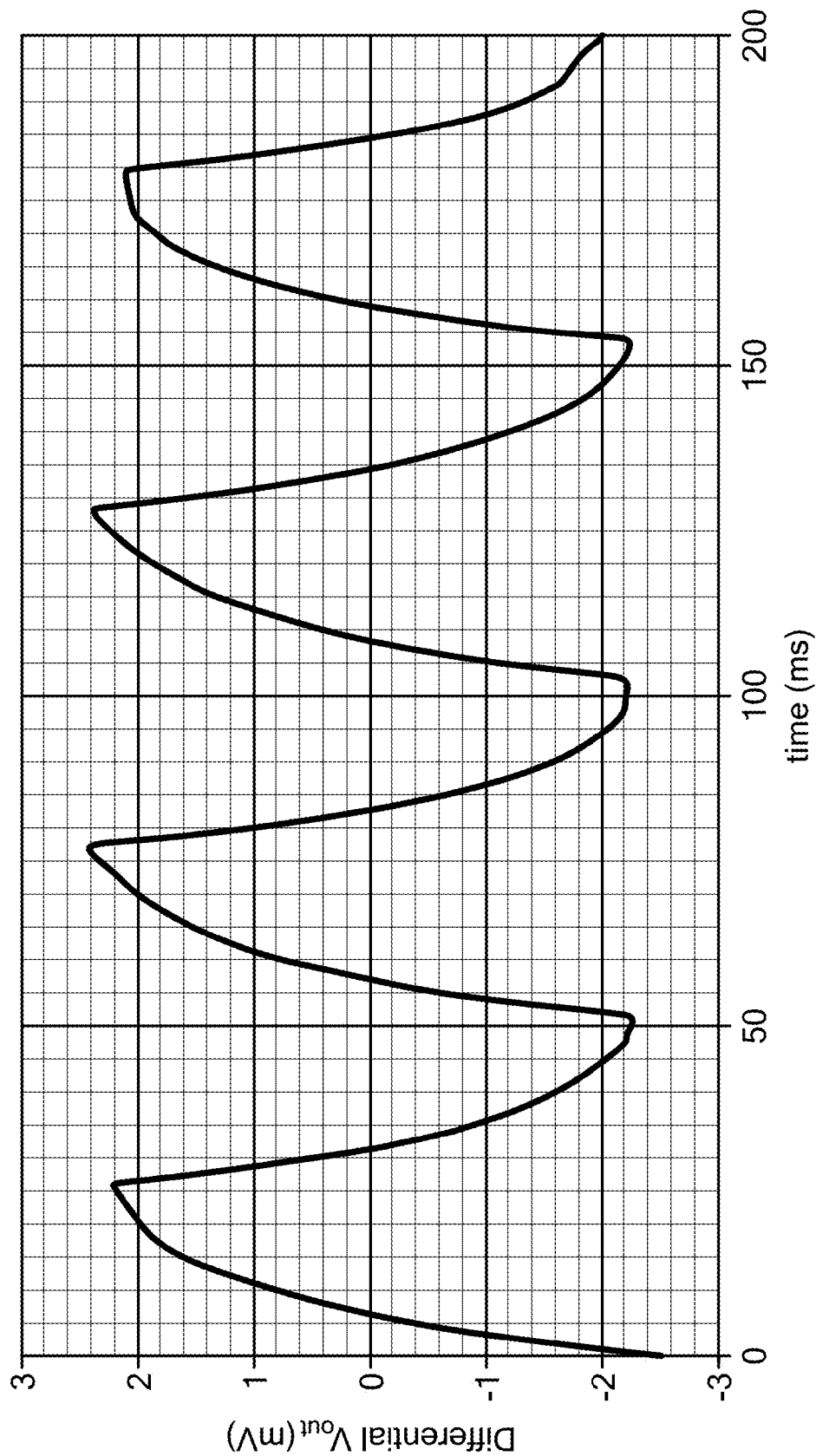
FIG. 12 illustrates simulated differential output voltage of a test signal generator with a load capacitance of 3 pF and enabled transient noise for all devices.

The OTA is preferably fully-differential to obtain a high power supply rejection ratio (PSRR) and common-mode rejection ratio (CMRR). Furthermore, common-mode interferences are suppressed by the instrumentation amplifier, which typically has a CMRR of more than 70 dB in biopotential measurement applications. For the ease of signal generation and amplitude detection with comparators (FIG. 9), a square wave input signal can be employed in this method, which results in a slewed waveform (FIG. 12) at the capacitively loaded OTA output and into an almost sinusoidal waveform at the LPF output due to the filtering (FIG. 10). The linearity of the OTA is not critical in this amplitude detection-based method, and a third-order harmonic distortion (HD3) specification of −20 dB is sufficient since it ensures that the OTA's HD3 remains below the third-order component of an ideal square wave.

Any suitable design of a sub-nano-Siemen OTA can be used. In one embodiment of the architecture, transistors $M_2$-$M_6$ in FIG. 11(a) implement a series-parallel current division with an 8:1 ratio. To generate precise picoampere range bias currents, a current splitting technique can be implemented as shown in FIG. 11(b) with N=10 and $I_{REF}$=150 nA. There is a trade-off between the requirements for high output impedance and low output-referred noise:

$$V_{n,out}^2 \approx \sum_{x=3}^{10} [V_{n,Mx}^2 \cdot (g_{m,Mx} \cdot R_o)^2], \quad (19)$$

where $R_o$ is the output impedance of the OTA. $M_x$ (x=3 to 10) are the transistors in output stage that have transconductances of $g_{m,Mx}$ and effective gate noises of $V_{n,Mx}^2$. To realize the required 25 pS transconductance at the OTA output stage, the bias current in the output stage would have to be in the picoampere range and the output impedance would be tens of gigaohms, which would generate integrated output noise of several millivolts. Thus, to avoid excessive output-referred noise, a common-gate structure ($M_8$-$M_{10}$) can be introduced, as shown in FIG. 11(a), which greatly reduces the output impedance with little impact on the bias current or transconductances of the transistors in the output stage ($M_3$-$M_7$). The bias network ($M_{11}$-$M_{20}$) utilizes scaled versions ($I_{b1}$, $I_{b4}$) of the reference current $I_{REF}$ in FIG. 11(b). With the added structure, the output impedance is lowered to approximately $1/g_m$ of transistor $M_8$. The OTA has a simulated output impedance of 2.9 GΩ and an integrated (0.01-100 Hz) output-referred noise of 78 μV. Since the output stage operates with a current of less than 20 pA and has an output resistance of 2.9 GΩ the simulated shift of the common-mode output voltage is less than 9.6 mV even with an excessive 20% mismatch between the pull-up and pull-down transistors. Hence, a common-mode feedback circuit is not necessary.

Figure 13:
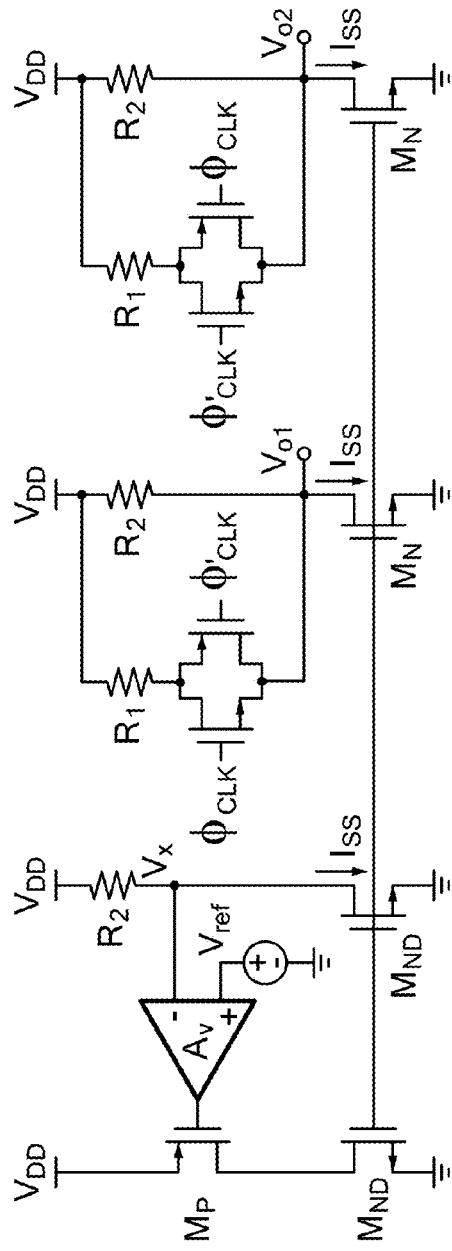
FIG. 13 illustrates an embodiment of a schematic of a differential voltage limiter.
Figure 14:
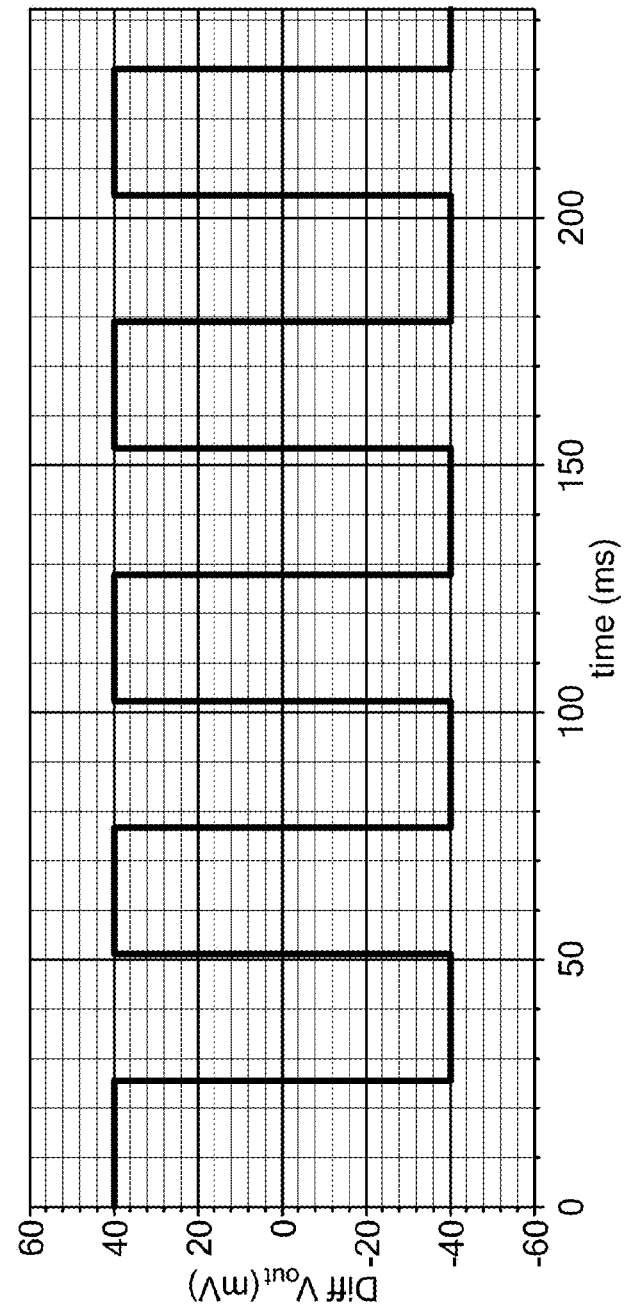
FIG. 14 illustrates a simulated differential output voltage ($v_{o1}-v_{o2}$) of the voltage limited (typical corner case, 27° C.)

Based on the simulated transconductance and noise of the OTA, the swing at its input should be limited to a differential peak-to-peak voltage of 80 mV. FIG. 13 displays an embodiment of a voltage limiter 66 suitable for this purpose. Its output signal level is changed by alternatively steering the current $I_{SS}$ into resistor $R_2$ (connected to $V_{o1}$) when the 19.5 Hz (20 KHz/1024) output signal ($\Phi_{CLK}$) of the frequency divider is low, or by steering $I_{SS}$ into the parallel combination of $R_1$ and $R_2$ when $\Phi_{CLK}$ is high. For the $V_{o2}$ branch, the operation is the same but with reversed clock signals at the switching transistors. The values of $R_1$, $R_2$ and $I_{SS}$ can be calculated based on the output voltage swing requirement, where the voltage drop is either $I_{SS} \cdot R_2$ or $I_{SS} \cdot (R_1 \| R_2)$. However, the use of large currents causes high power consumption, while the use of large resistors results in large layout area. In the presented design, a current of 100 μA was chosen in combination with $R_1$=82 KΩ and $R_2$=6.15 KΩ. The output DC level of the limiter can also be controlled with the values of $R_1$, $R_2$, and $I_{SS}$. Since the input DC level of the OTA is 600 mV, the component values are chosen such that the limiter output signal levels at $V_{o1}$ and $V_{o2}$ range from 580 mV to 620 mV. Transmission gates are used as switches to minimize the resistance in series with $R_1$ when the switches are closed. FIG. 14 shows the transient differential output voltage swing of the limiter, which has a peak-to-peak value close to 80 mV.

The amplitude of the limiter output should exhibit as little variation as possible under different process corner and temperature conditions. As depicted in FIG. 13, a regulation loop with a differential amplifier is added, in which a dummy transistor $M_{ND}$ has the same dimensions as transistor $M_N$, such that the voltage at node $V_X$ reflects the variations of $R_2$ and $M_N$ in the main branches because the transistors have the same gate and source voltages. Any suitable amplifier can be used for this loop. The negative feedback loop adjusts the gate voltage of $M_{ND}$ such that its drain-to-source voltage is driven to a value close to $v_{ref}$=580 mV. When $M_N$, $M_{ND}$, and all resistors are realized with multiple sub-devices that are matched through proper layout, then the $I_{SS} \cdot R_2$ product only has a small error between the branches and the drain-to-source voltage of $M_N$ is also equal to $V_{ref}$ (580 mV) when $R_1$ is disconnected. Furthermore, the difference between the minimum and maximum output voltages depends on the ratio of the matched resistors, and has a reliable maximum value that is 40 mV higher when the switch in a branch is closed. Consequently, the peak-to-peak differential output signal swing ($V_{o1}$-$V_{o2}$) is always close to 80 mV.

Figure 15:
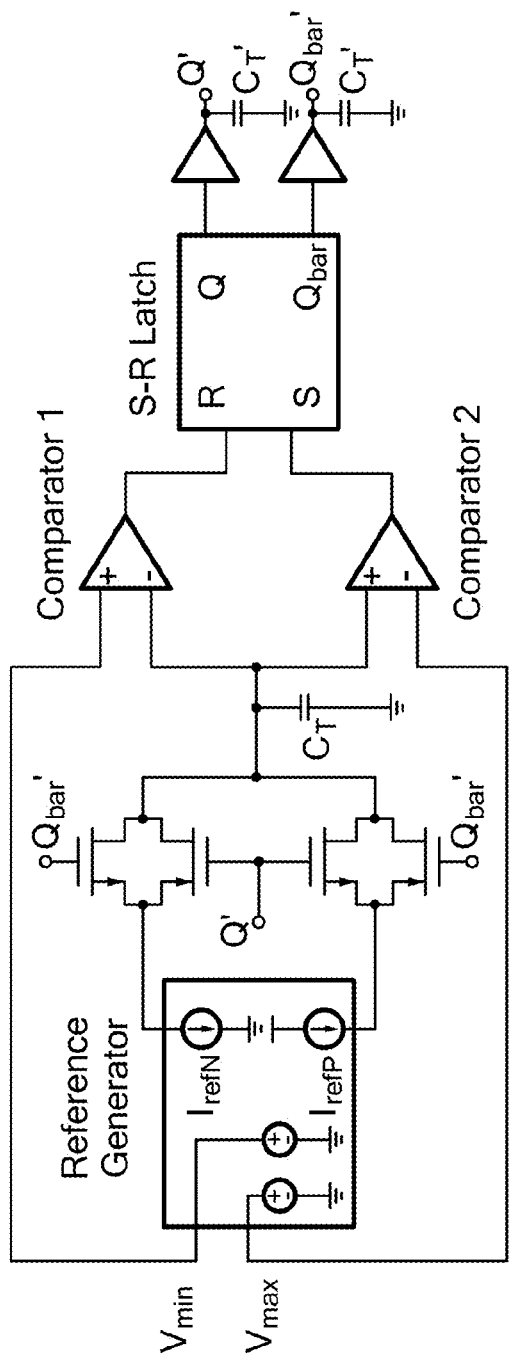
FIG. 15 illustrates an embodiment of a relaxation oscillator block diagram.
Figure 16:
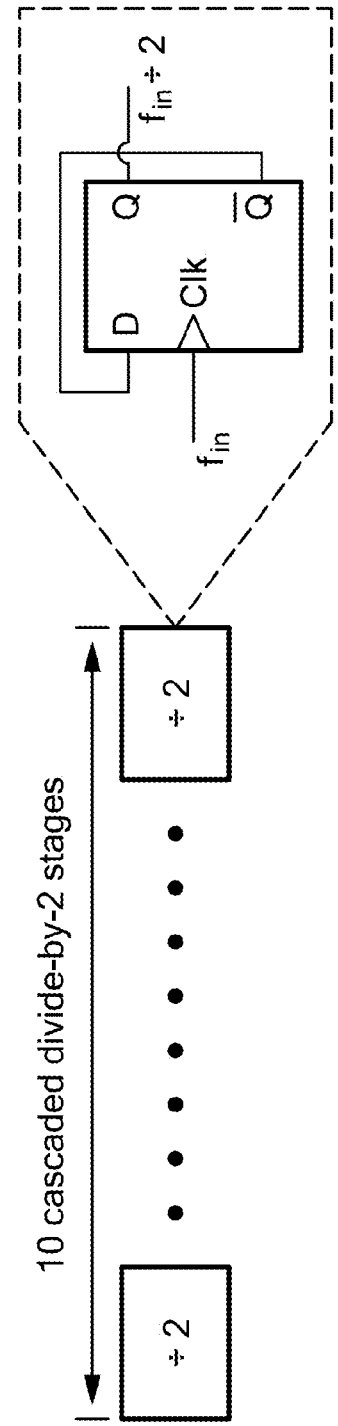
FIG. 16 illustrates a frequency divider (with standard D flip-flops)

The test clock signal can be generated with any suitable relaxation oscillator. FIG. 15 illustrates a block diagram for one suitable relaxation oscillator 62. The oscillator achieves a power consumption of 4.9 μW with 1.2 V power supply and a temperature coefficient of 314 ppm/° C. The divide-by-1024 operation is implemented through 10 cascaded divide-by-2 stages consisting of D flip-flops with feedback as shown in FIG. 16.

Test Current Generation Simulation Results

Figure 17:
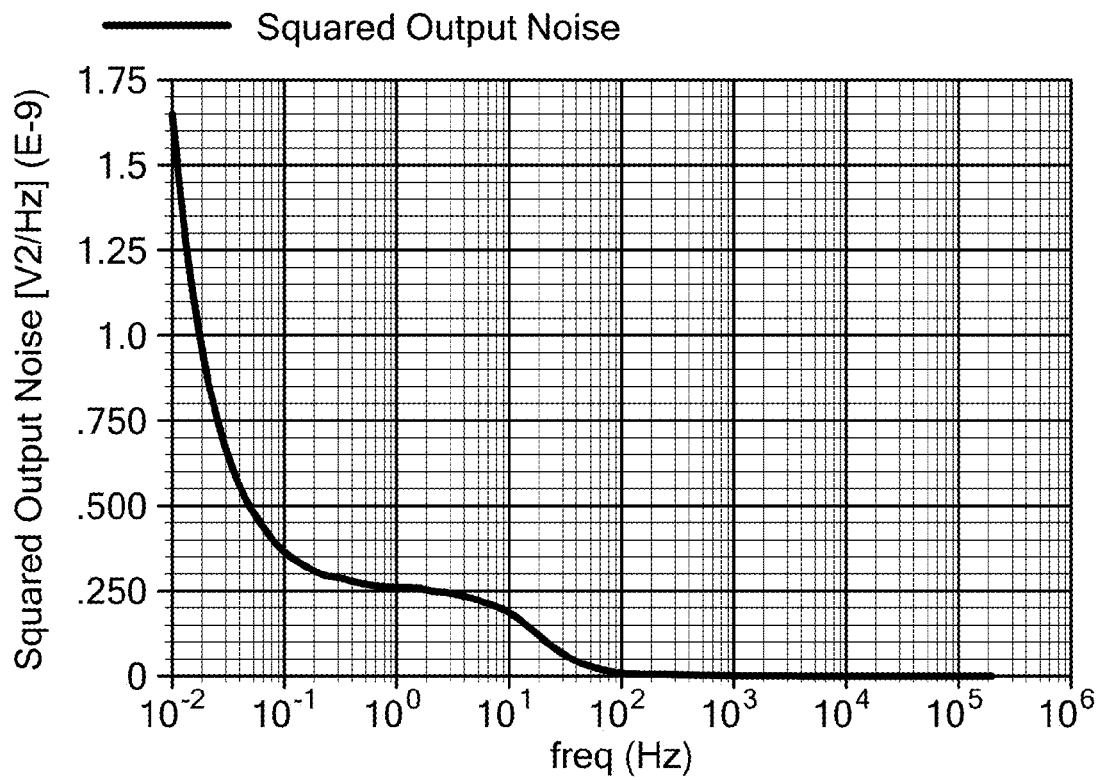
FIG. 17 illustrates squared output noise of a test signal generator vs. frequency.
Figure 18:
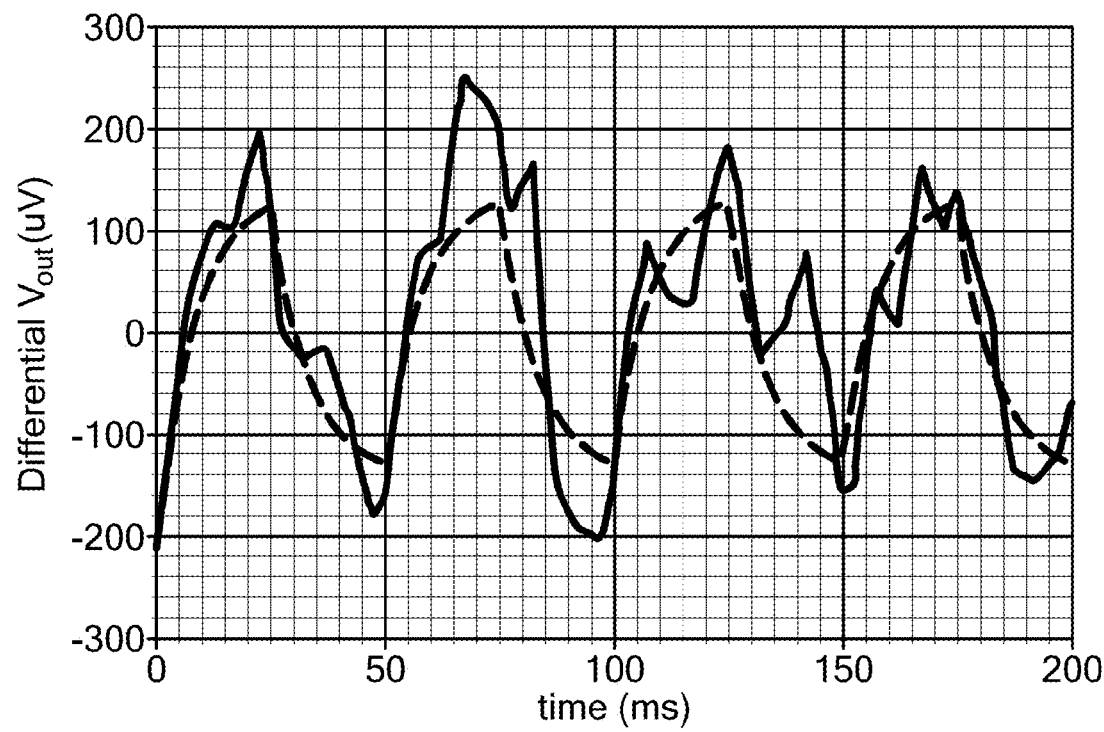
FIG. 18 illustrates simulated effect of transient noise with small OTA output voltage amplitude (the dashed line is the ideal output signal without noise)
Figure 19A:
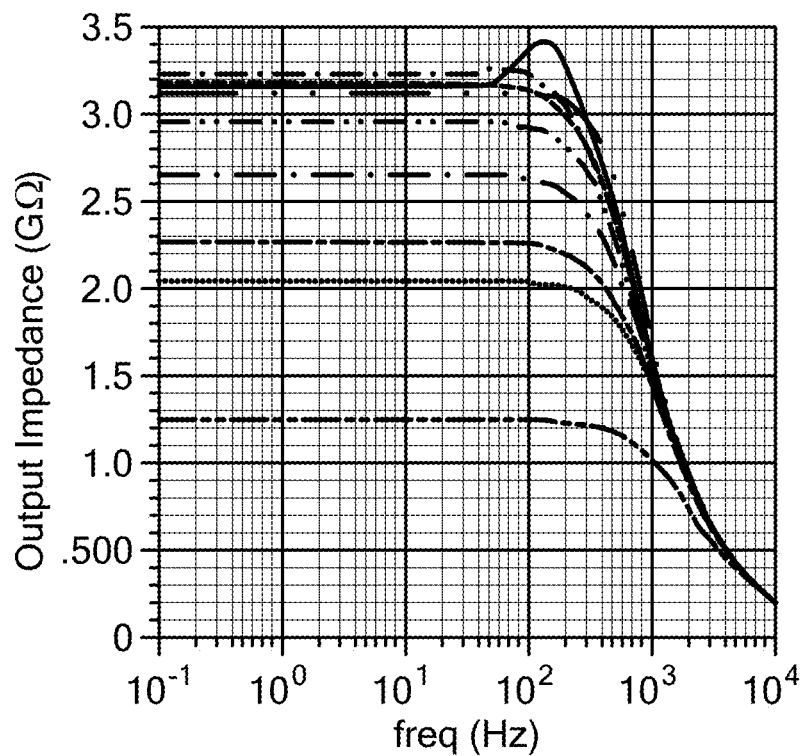
FIGS. 19(a) and 19(b) illustrate simulated output impedance and transconductance respectively of the OTA for corners (ff, tt, ss) with different temperatures (−30° C., 27° C., 85° C.) (the bolded line is the typical corner case at 27° C.)
Figure 19B:
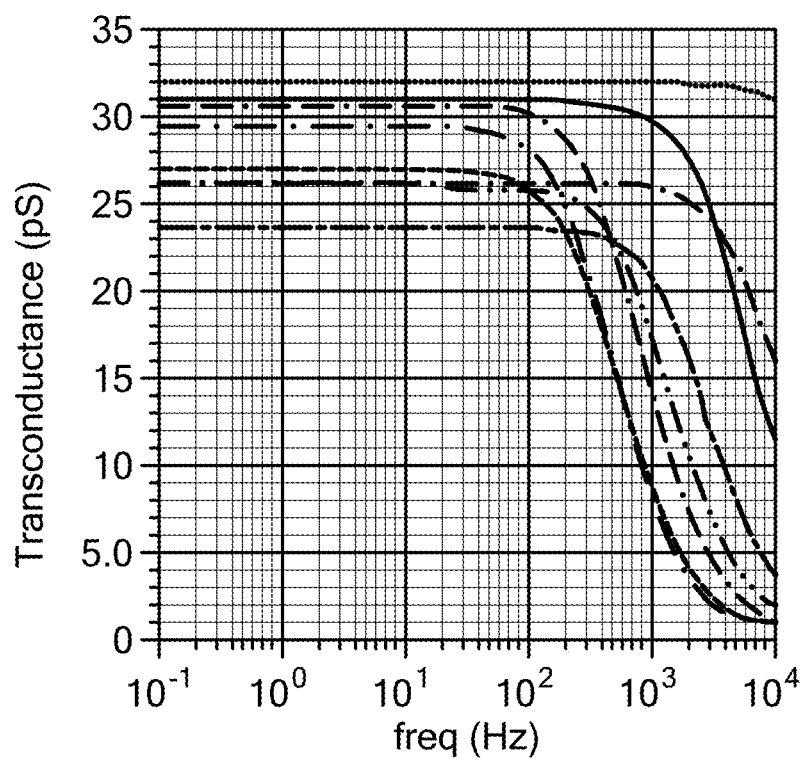

The test current generation circuitry described above was designed and simulated using 0.13 μm CMOS technology with 1.2V supply. Since the test signal generator was designed for amplitude-based detection, the effects of process and temperature variations on key parameters were evaluated with foundry-supplied device models. Table 3 summarizes the simulation results for the OTA. FIG. 17 shows the squared output noise of the test signal generator with a load capacitance of 3 pF. FIG. 18 shows a noise-limited scenario, in which the simulated output noise significantly degrades the voltage amplitude at the instrumentation amplifier input. For this reason, the voltage amplitude at the OTA input was raised to an 80 mV differential peak-to-peak value, resulting in the instrumentation amplifier input voltage swing with high signal-to-noise ratio in FIG. 12. FIGS. 19(a) and 19(b) show the OTA's output impedance and transconductance vs. frequency for different process corner cases and temperatures. The output impedance remains above 1 GΩ up to 100 Hz, and the variation of the transconductance is approximately 20% in the worst case, which is acceptable if the reference voltages of the comparator bank (FIG. 10) are chosen to cover the anticipated worst case. Table 4 reveals that the phase margin of the negative feedback loop in FIG. 13 is always higher than 60°, ensuring the stability of the circuit. The worst amplitude error (3.2%) of the limiter occurs in the slow corner case at 85° C. Depending on the layout quality, an additional error of 1-3% could be introduced due to device mismatches. However, a worst-case total amplitude error of less than 6% could be acceptable, depending on the application.

TABLE 3

OTA SIMULATED RESULTS

| Performance | OTA |
| --- | --- |
| Output impedance at 100 Hz | 2.9 GΩ |
| Transconductance | 25.9 pS |
| Output-referred noise, 0.01 Hz-100 Hz | 78 µV |
| HD3 (of $i_{out}$, sinusoidal $V_{in}$ = 80 m$V_{p-p}$ at 19.5 Hz) | −30.1 dB |
| CMRR mean/standard deviation (with mismatch*) | 69 dB/7.2 dB |
| PSRR mean/standard deviation (with mismatch*) | 56 dB/6.5 dB |
| Supply current | 168 nA |

*100 Monte Carlo simulations with a load capacitance of 3 pF at 60 Hz.

TABLE 4

SIMULATED DIFFERENTIAL OUTPUT VOLTAGE SWING OF THE LIMITER AND PHASE MARGIN IN ITS REGULATION LOOP

| Process | Temperature | Differential Output Swing (mV) | Phase Margin |
| --- | --- | --- | --- |
| Typical | −30° C. | 81.1 mV | 64.3 deg. |
|  | 27° C. | 80.4 mV | 68.9 deg. |
|  | 85° C. | 79.2 mV | 72.8 deg. |
| Fast | −30° C. | 82.2 mV | 65.4 deg. |
|  | 27° C. | 81.0 mV | 70.2 deg. |
|  | 85° C. | 78.6 mV | 73.9 deg. |
| Slow | −30° C. | 78.4 mV | 64.1 deg. |
|  | 27° C. | 78.4 mV | 68.7 deg. |
|  | 85° C. | 77.8 mV | 72.4 deg. |

Figure 24:
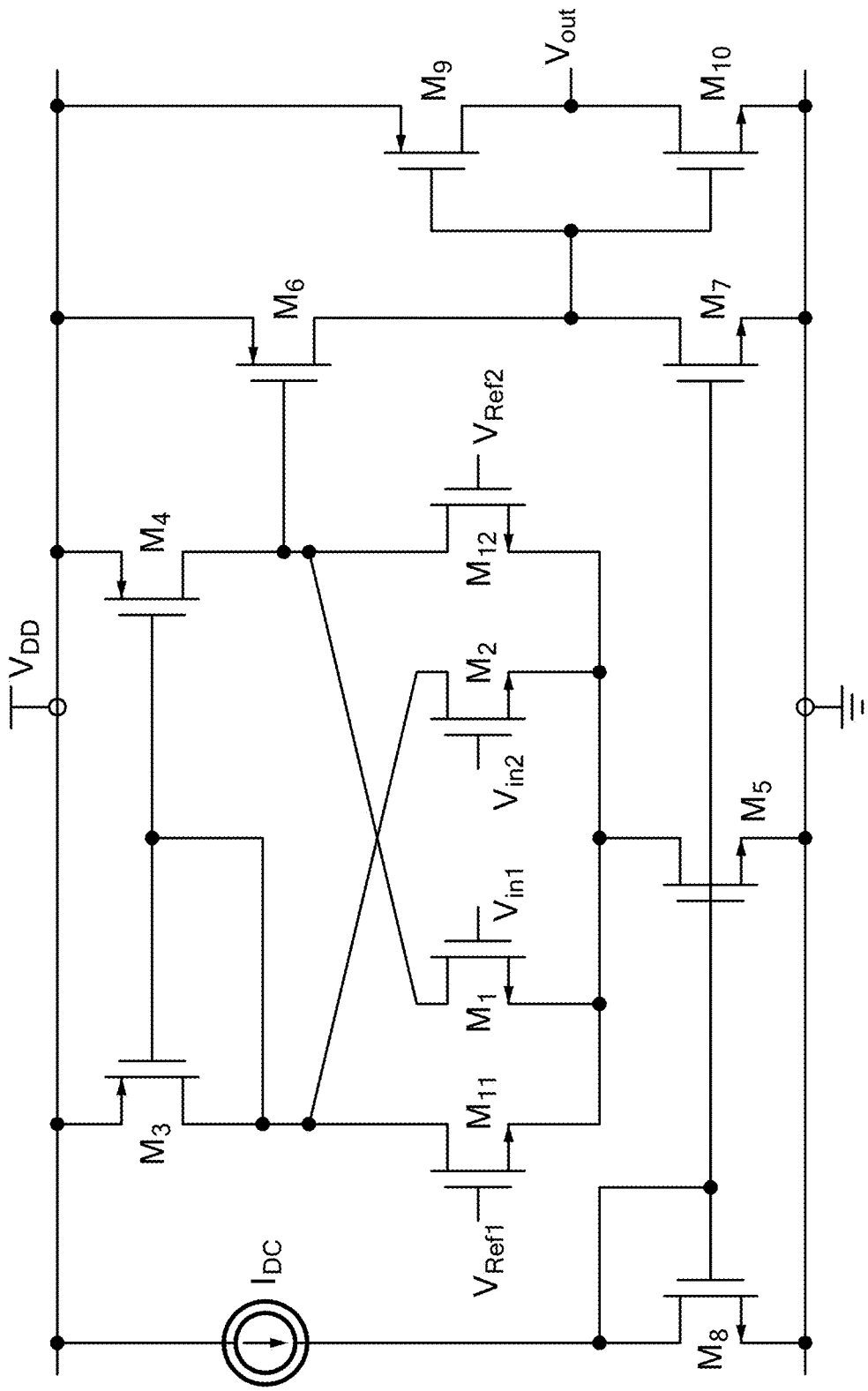
FIG. 24 is a schematic of an embodiment of a comparator used in the calibration circuit.
Figures 25A, 25B:
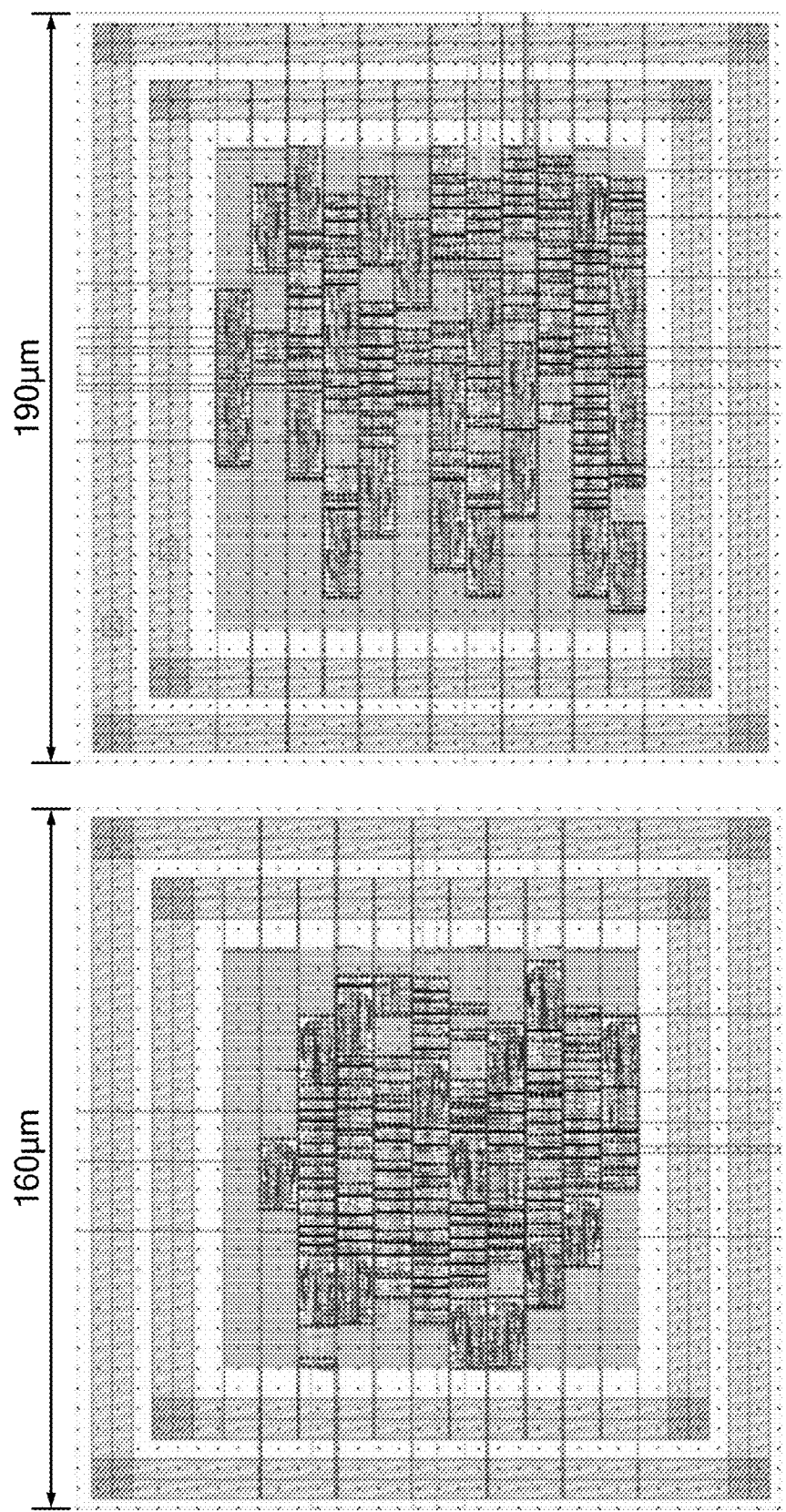
FIG. 25 illustrates a layout of a digital calibration unit in 130 nm CMOS technology: (a) control block, (b) memory block.

One embodiment of a calibration circuit is now described with reference to FIGS. 8 and 20-26. Referring to FIG. 8, an embodiment of the calibration circuit includes a test amplifier 32 (FIG. 23) connected to the output of the instrumentation amplifier or to gain or filtering stages downstream of the instrument amplifier. The test amplifier provides amplified input voltage signals to a bank of comparators (designed as depicted in FIG. 24) that in turn provides input signals to a calibration unit 30 including processor control and memory (FIG. 21). An oscillation detection unit 36 is operative to detect oscillation events at the output of the instrumentation amplifier and provide a signal indicative of the oscillation event to the calibration unit. The calibration unit is operative to compare measured voltage amplitudes from the instrumentation amplifier to a plurality of reference voltages from the comparator bank 34 and to generate a plurality of control signals response to the comparison, as described further below. The control signals are transmitted to the programmable capacitors (FIG. 4) of the instrumentation amplifier to optimize the negative capacitance generated at the IA's input.

Figure 20:
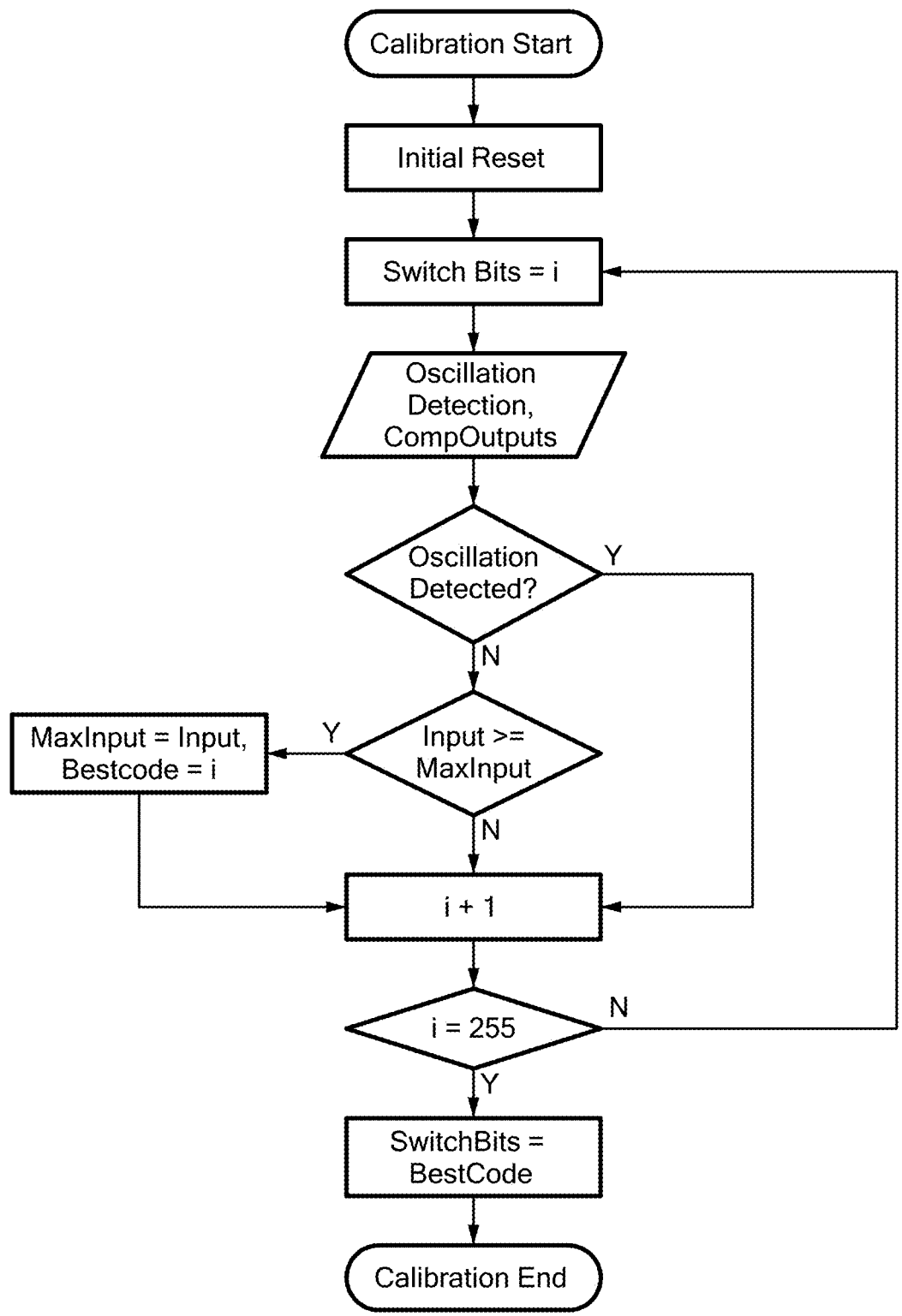
FIG. 20 is a schematic flowchart illustrating an embodiment of a calibration process.
Figure 21:
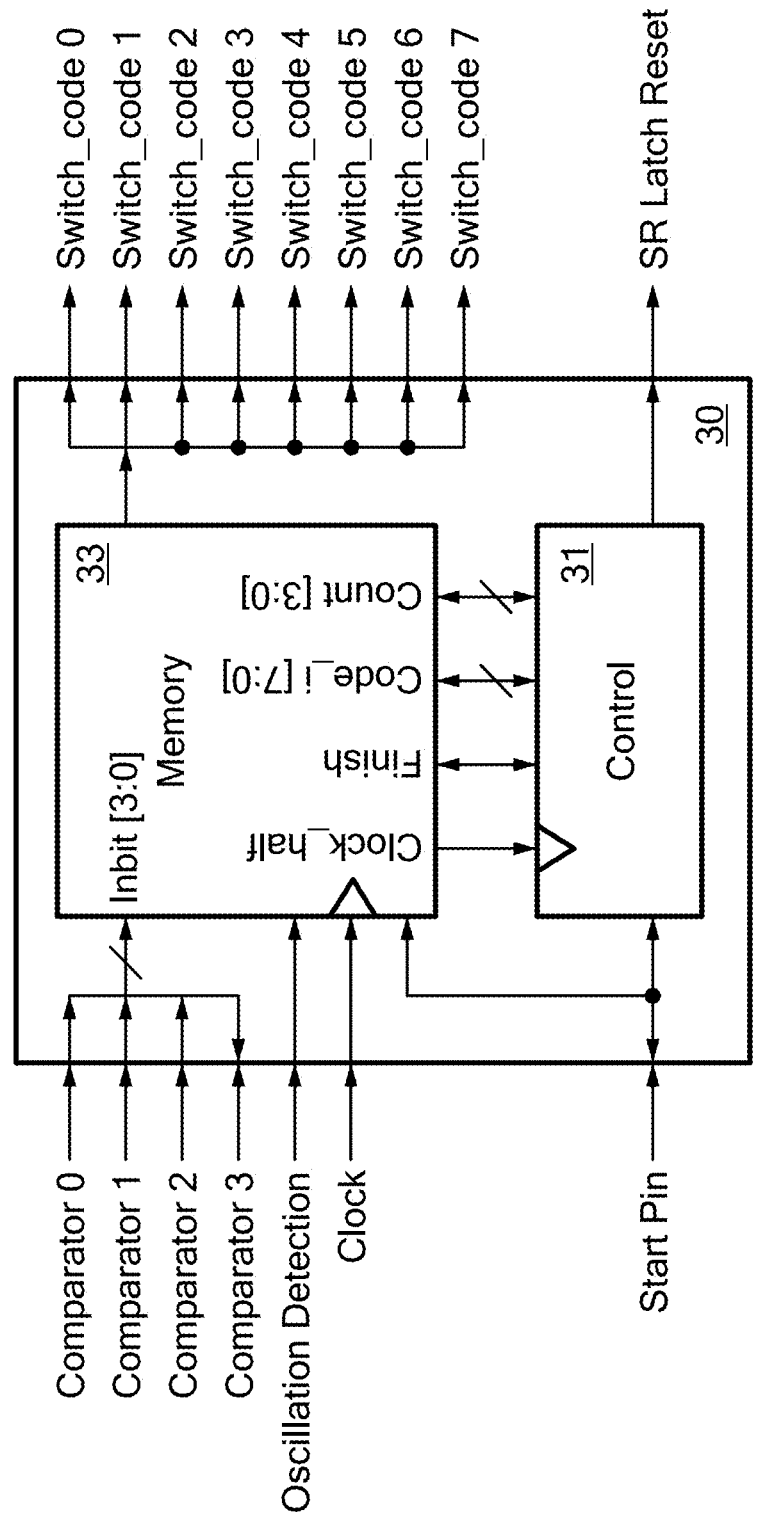
FIG. 21 is a schematic block diagram of an embodiment of a digital calibration unit.

An embodiment of a digital calibration process is depicted as a flowchart in FIG. 20. A start signal resets all registers at the beginning of the calibration process. The functions of setting the control signals for switches, decision-making, and saving the desired values in memory are completed during each cycle of the process. The calibration unit is implemented by control block 31 and memory block 33 shown in FIG. 21. At each step, the calibration unit first sends a reset signal to all the SR latches located at the outputs of the comparators. Then it sets the 8 control signals that are connected to the switches ($S_7$-$S_0$) of the IA's negative capacitance generation block, where the initial output code (switch_code[7:0]) is "00000000". After waiting for 7 periods of the test signal to allow for settling of the analog signals, the reset signal goes to "0" and the SR latches hold the output values of the four comparators from which the test signal amplitude can be inferred (inbit[3:0]). If the oscillation detection bit is "1", then the unit will ignore inbit[3:0] and increase the current switch_code by one. If there is no oscillation, then inbit[3:0] is compared with the max_code (initially zero). If inbit[3:0] is equal or larger than max_code, then its value is replaced with max_code in the memory. Furthermore, the related switch_code is saved as best_code in another memory location. Afterwards, the switch_code is incremented by one, and the process is repeated. When the switch_code reaches "11111111" (255 in decimal), then the calibration unit reads the best_code from the memory and applies the corresponding switch_code to the programmable capacitor bank at the IA for optimum impedance at the end of the calibration. The optimum code is applied to the IA's capacitor bank until the calibration is restarted after changing electrode cables.

FIG. 21 shows a diagram of the calibration unit 30 with its input/output ports. The memory block receives the latched outputs of the comparators as inputs. It generates and saves the 8-bit codes to control the switches in the capacitor bank. The main clock for the calibration block is derived from the same oscillator that is part of the test signal generation circuitry (see FIG. 8). The calibration unit uses a clock that is two times faster than the 19.5 Hz test signal. Such low clock speed is sufficient for this application since the test signal has a very low frequency and the calibration block has to wait proportionally to make decisions. The control block works with an internal clock signal (clock_half) generated by the memory block with half the frequency of the main clock. The internal frequency divider is implemented with a 1-bit counter inside of the memory block. The memory cells in the memory block are built by shift registers. Each of the flip-flops in the shift registers imitates the function of an SRAM cell. Therefore, the memory cells require address, read and write signals based on SRAM principles. The code comparisons and final decision-making tasks are also performed in the memory block.

The control block 31 contains a 4-bit counter to count the number of test signal cycles after changing the switch_code, which ensures sufficient settling time for the analog signals. The control block also has an 8-bit counter to generate all 256 states of the switch controls, which is sent to the memory block 33 as code_i[7:0] and also sent out as the switch_code for both capacitor banks of the IA (see FIG. 22). The reset signal that is needed to reset the SR latches is generated by the control block during each calibration step. At the end, a finish signal is sent to the memory block 33 from the control block to stop the calibration process. Afterwards, the switch_code will be set to the optimum value and will remain unaltered.

Figure 22:
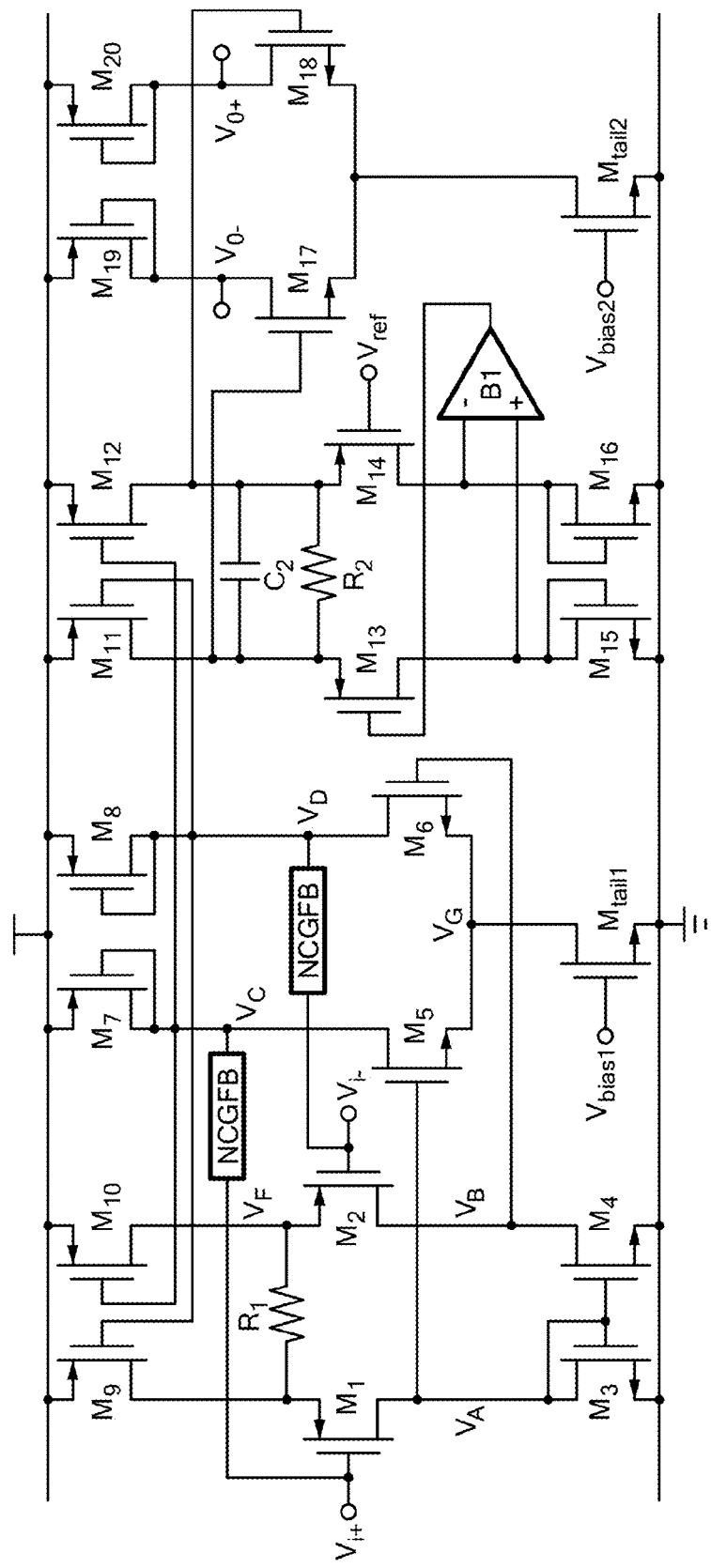
FIG. 22 is a circuit diagram of an embodiment of an instrumentation amplifier with negative capacitance generation feedback.
Figure 23:
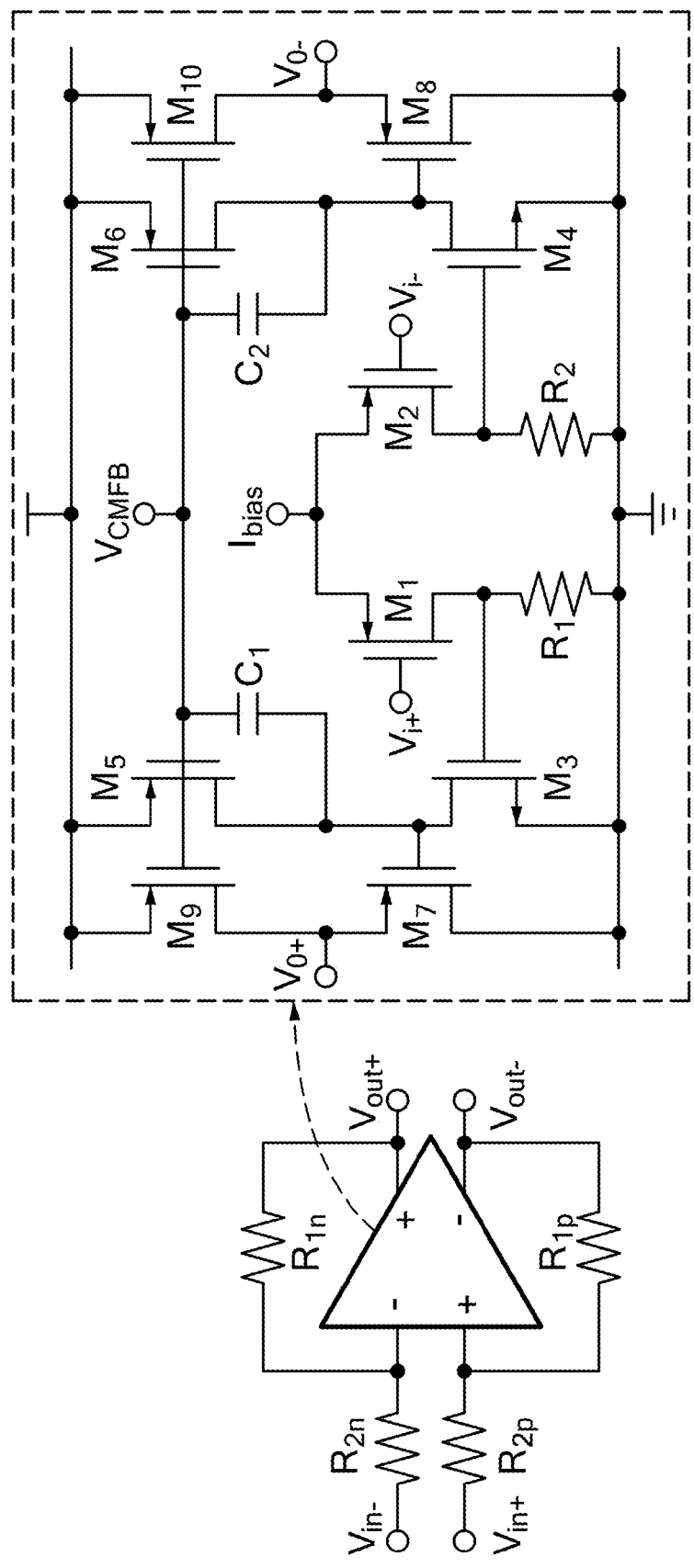
FIG. 23 is a circuit diagram of an embodiment of a test amplifier used in the calibration circuit.

FIG. 22 shows an embodiment of an IA schematic and the programmable capacitors that form a negative capacitance generation feedback (NCGFB), generally as described above, which is automatically controlled by the digital calibration unit. Because the IA circuit is not perfectly symmetric (i.e., $M_3$ is diode-connected while $M_4$ is not), it can be observed that the optimum result can be achieved by setting the capacitor sizes in the negative path ($C_n$) to around half of the sizes of the positive path ($C_p$). The tuning range of the 8-bit capacitor networks should be designed to compensate for the 50-150 pF capacitances from the cables and PCB by generating negative capacitance at the IA input. The switches of the both capacitor banks (see FIG. 5) receive the same control signals from the calibration unit.

Depending on the value of the parasitic capacitances, the input capacitance may be overcompensated through the generation of a negative capacitance that is too large (i.e., when the value of switch_code is too high). Actually, as the values of the programmable capacitors are concurrently increased, the best code is the last code before oscillation occurs. With a test input current amplitude of $i_t$=0.5 pA and 20 dB of gain in the IA and filter combination, the voltage swings at the filter output are below 25 mV across process corner cases. Simulations also revealed that the oscillations have amplitudes at the IA output that are at least three times higher, such that an oscillation detection threshold can be set at twice the maximum signal swing during stable operation. As indicated in FIG. 8, an oscillation detection comparator is connected at the output of the instrumentation amplifier to check for oscillation events during each iteration in the calibration unit. The calibration method (FIG. 20) ignores the codes that lead to oscillation. All capacitor switch bank settings are tested during the calibration. Thus, only one code is skipped in case the oscillation detector threshold is exceeded due to an unexpected noise source. Choosing the number of bits for the programmable capacitors such that multiple codes meet the minimum input impedance requirement makes the calibration scheme more reliable. In addition, multiple comparators were placed instead of a single comparator to test if the output amplitude is high enough to meet the minimum impedance requirement. To account for the different corner cases and temperature conditions, the input impedance of the IA was set to 500 MΩ to obtain the range of output differential amplitudes. Afterwards, the differential reference levels were defined for the comparators as three equally-spaced values (300 mV$_{p-p}$, 200 mV$_{p-p}$, 100 mV$_{p-p}$) and one additional (40 mV$_{p-p}$) to cover the range with some extra margin below the minimum The delay times are 8 periods of the test signal to allow settling after setting each code; and 2 more periods to compare the new input with previous one in memory, save the results in memory (if needed) and resetting the SR latches. Hence, it takes a total of 10 periods (around 510 ms with a 19.5 Hz test signal) per step, and around 130 s to finish the complete calibration. Note that cable changes are expected to be infrequent, making the wait time acceptable when the calibration is only initiated by the user from time to time.

An embodiment of the test amplifier in FIG. 8 has been designed with a gain of 20 in a prototype system. As displayed in FIG. 23, in one embodiment, the amplifier can be implemented with an operational amplifier (low-frequency gain of 41 dB, −3 dB corner frequency of 870 KHz, power consumption of 149 μW) in fully-differential configuration using feedback resistors of 11.17 MΩ and 447 K. With high-resistance polysilicon the layout area of the larger resistor would be 77 μm×140 μm, which is acceptable. The common-mode level at the output of the test amplifier is set to 650 mV. In the main signal path, the transistor-level IA design above was employed together with an adapted version (same architecture) of the filter.

Each comparator in the calibration path (FIG. 8) has a propagation delay of 20 μs and 300 μV input-referred offset while consuming 3 μW of power. FIG. 24 shows an embodiment of the comparator's schematic.

To implement the calibration system on a chip, synthesizable Verilog HDL codes were written for the two digital blocks. All required unit cells were designed and laid out in 130 nm CMOS technology. The Verilog code was synthesized to gate-level netlists with Cadence RTL Complier. Cadence Encounter was used to automatically place and route the layouts from the generated gate-level netlists. The layout of the calibration unit is displayed in FIG. 25. It occupies a total chip area of approximately 0.062 mm² in 130 nm CMOS technology. The total power consumption of the digital calibration unit at the main clock frequency of 39 Hz is 1.2 μW with 1.2 V supply voltage. A summary of the digital calibration unit specifications is given in Table 5.

TABLE 5

DIGITAL CALIBRATION UNIT SUMMARY

| Block | Number of Gates | Area | Power |
|---|---|---|---|
| Control | 113 | 0.026 mm² | — |
| Memory | 146 | 0.036 mm² | — |
| Total | 259 | 0.062 mm² | 1.2 μW |

Calibration Simulation Results

The transistor-level analog EEG front-end blocks and the Verilog HDL codes of calibration unit were evaluated together with Cadence AMS simulations. Furthermore, Cadence Spectre simulations were performed using the transistor-level synthesized version of the calibration unit (by itself) to verify that the outcome matches the results with the functional code. Finally, a post-layout simulation of the standalone calibration unit was performed to confirm that the outputs match the schematic and functional (Verilog HDL) simulations.

Figure 26:
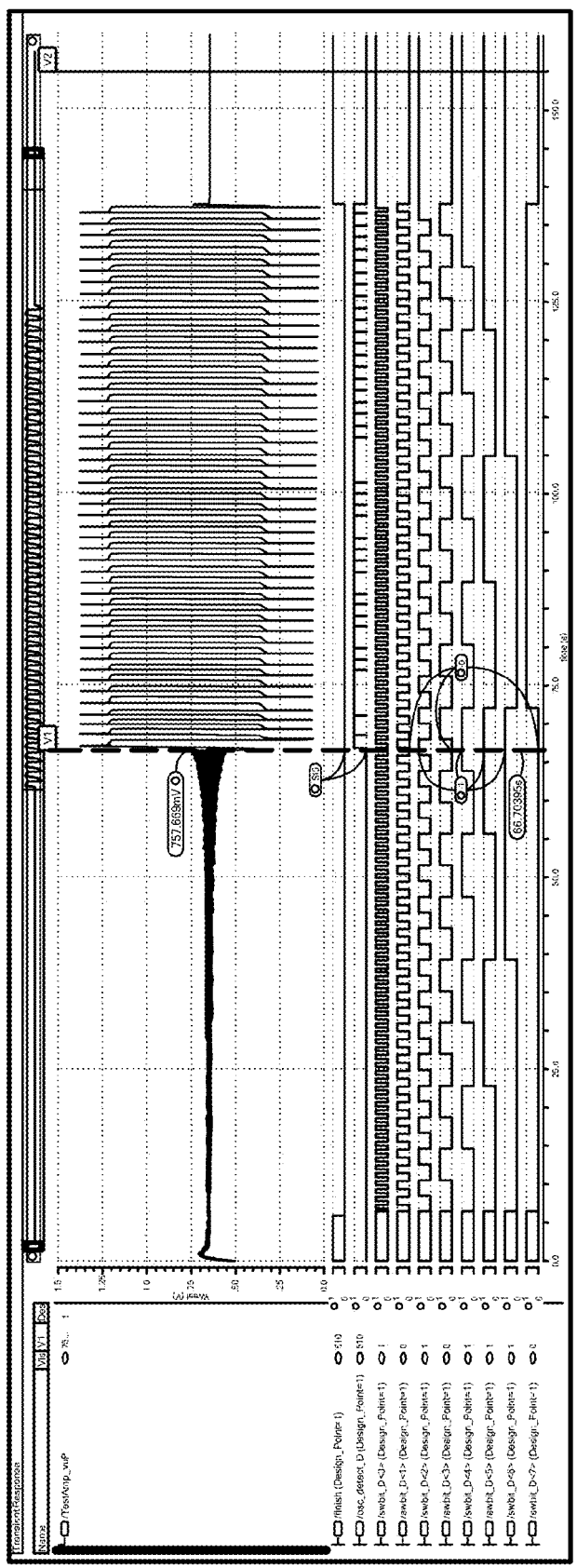
FIG. 26 illustrates simulated waveforms of a test amplifier output and the digital control signals for capacitor bank switches ($C_{inn}=C_{inp}=100$ pF).

FIG. 26 shows the Cadence output waveforms of the test amplifier and the digital signals that control the switches in the capacitor bank. The test current generator is disconnected when the "finish" signal (the topmost digital signal in the figure) transitions to high. If oscillation occurs as in FIG. 26, then the oscillation detection bit (second digital signal from the top) is set to "1". In this case, the calibration block saves the best code without oscillation and sets the switches to it after cycling through all combinations. In the typical process corner case with parasitic capacitances ($C_{inp}$ and $C_{inn}$ in FIG. 8) at the IA input both equal to 100 pF, the best code identified by the calibration system is "01010111". With this code, the simulated input impedance is equal to 2.2 GΩ at 50 Hz. Table 6 lists simulation results of an EEG front-end with the calibration unit for other process corner cases and parasitic input capacitances in the 50-150 pF range. In all cases, the simulated input impedance of the IA remains above the 500 MΩ target for dry-contact EEG measurement methods.

TABLE 6

SIMULATION RESULTS FOR DIFFERENT PARASITIC CAPACITANCE VALUES AND PROCESS CORNERS

| $C_{inp}$, $C_{inn}$ (in FIG. 1) | Switch Control Code ($S_{x7}$-$S_{x0}$ in FIG. 4) | Process Corner | IA Input Impedance |
|---|---|---|---|
| 150 pF, 150 pF | 10011001 | SS | 1.12 GΩ |
| 150 pF, 150 pF | 10101101 | TT | 1.90 GΩ |
| 150 pF, 150 pF | 10111111 | FF | 2.34 GΩ |
| 150 pF, 100 pF | 01011111 | SS | 669 MΩ |
| 150 pF, 100 pF | 01110101 | TT | 1.28 GΩ |
| 150 pF, 100 pF | 01111111 | FF | 873 MΩ |
| 100 pF, 100 pF | 01001001 | SS | 1.33 GΩ |
| 100 pF, 100 pF | 01010111 | TT | 2.20 GΩ |
| 100 pF, 100 pF | 01011111 | FF | 1.47 GΩ |
| 100 pF, 50 pF | 00001101 | SS | 859 MΩ |
| 100 pF, 50 pF | 00011011 | TT | 1.53 GΩ |
| 100 pF, 50 pF | 00100101 | FF | 1.70 GΩ |
| 50 pF, 50 pF | 00000000 | SS | 10.30 GΩ |
| 50 pF, 50 pF | 00000001 | TT | 2.77 GΩ |
| 50 pF, 50 pF | 00000111 | FF | 2.49 GΩ |

It will be appreciated that the various features of the embodiments described herein can be combined in a variety of ways. For example, a feature described in conjunction with one embodiment may be included in another embodiment even if not explicitly described in conjunction with that embodiment.

The present invention has been described with reference to the preferred embodiments. It is to be understood that the invention is not limited to the exact details of construction, operation, exact materials or embodiments shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

The calibration system and method can be implemented on the same chip as the IA. In one embodiment, calibration can be activated by a user of the application of which the IA with calibration is a part. For example, upon changing electrode cables, the calibration can be activated. The activation can be performed in any suitable manner, such as by a button or switch, or through a graphical or other computer-implemented interface with the application. The activation can be performed automatically, for example, upon detection of an event such as connection of new cables.

It will be appreciated that the calibration circuit illustrated by the ADC and DSP in FIG. 1 can be implemented in a variety of ways in addition to the particular implementations described with reference to FIGS. 8-26. Similarly, the instrumentation amplifier 12 of FIG. 1 can be implemented in other ways in addition to the particular implementation described above. Also, while the instrumentation amplifier circuit has been described as particularly appropriate for biosensing measurements, it will be appropriated that the circuit and method can be used for other applications for which input impedance boosting would be desirable.

It will be appreciated that the various features of the embodiments described herein can be combined in a variety of ways. For example, a feature described in conjunction with one embodiment may be included in another embodiment even if not explicitly described in conjunction with that embodiment.

REFERENCES

[1] R. F. Yazicioglu, P. Merken, R. Puers, and C. Van Hoof, "A 60 µW 60 nV/°Hz readout front-end for portable biopotential acquisition systems," *IEEE J. Solid-State Circuits*, vol. 42, no. 5, pp. 1100-1110, May 2007.

[2] N. Verma, A. Shoeb, J. Bohorquez, J Dawson, J. Guttag, and A. P. Chandrakasan, "A micro-power EEG acquisition SoC with integrated feature extraction processor for a chronic seizure detection system," *IEEE J. Solid-State Circuits*, vol. 45, no. 4, pp. 804-816, April 2010.

[3] J. Xu, R. F. Yazicioglu, P. Harpe, K. A. A. Makinwa, and C. Van Hoof, "A 160 µW 8-channel active electrode system for EEG," in *IEEE Intl. Solid-State Circuits Conf. (ISSCC) Dig. Tech. Papers*, pp. 300-302, February 2011.

[4] A. Casson, D. Yates, S. Smith, J. Duncan, and E. Rodriguez-Villegas, "Wearable electroencephalography," *IEEE Engineering in Medicine and Biology Magazine*, vol. 29, no. 3, pp. 44-56, May-June 2010.

[5] Y. M. Chi, T.-P. Jung, and G. Cauwenberghs, "Dry-contact and noncontact biopotential electrodes: methodological review," *IEEE Reviews in Biomedical Engineering*, vol. 3, no. 1, pp. 106-119, October 2010.

[6] C. Assambo and M. J. Burke, "Amplifier input impedance in dry electrode ECG recording," in *Proc. Annual IEEE Conf. Engineering in Medicine and Biology Society (EMBC)*, pp. 1774-1777, September 2009.

[7] K. Soundararajan and K. Ramakrishna, "Nonideal negative resistors and capacitors using an operational amplifier," *IEEE Trans. on Circuits and Systems*, vol. 22, no. 9, pp. 760-763, September 1975.

[8] R. Martins, S. Selberherr, and F. A. Vaz, "A CMOS IC for portable EEG acquisition systems," *IEEE Trans. on Instrumentation and Measurement*, vol. 47, no. 5, pp. 1191-1196, October 1998.

[9] A. Worapishet, A. Demosthenous, and X. Liu, "A CMOS instrumentation amplifier with 90-dB CMRR at 2-MHz using capacitive neutralization: analysis, design considerations, and implementation," *IEEE Trans. on Circuits and Systems-I: Regular Papers*, vol. 58, no. 4, pp. 699-710, April. 2011.

[10] Analog Devices. *Precision Instrumentation Amplifier-AD8221*. Online: http://www.analog.com/static/imported-files/data_sheets/AD8221.pdf

[11] Q. Fan, F. Sebastian, J. H. Huijsing, and K. A. A. Makinwa, "A 1.8 µW 60 nV/√Hz capacitively-coupled chopper instrumentation amplifier in 65 nm CMOS for wireless sensor nodes," *IEEE J. Solid-State Circuits*, vol. 46, no. 7, pp. 1534-1543, July 2011.

[12] A. I. Larky, "Negative-impedance converters," *IRE Trans. Circuit Theory*, vol. 4, no. 3, pp. 124-131, September 1957.

[13] Yan Li, Carmen C. Y. Poon, and Yuan-Ting Zhang, "Analog integrated circuits design for processing Physiological Signals," *IEEE Reviews in Biomedical Engineering*, vol. 3, pp. 93-105, 2010.

[14] A. Arnaud, R. Fiorelli, and C. Galup-Montoro, "Nanowatt, sub-nS OTAs, with sub-10-mV input offset, using series-parallel current Mirrors," *IEEE J. Solid-State Circuits*, vol. 41, no. 9, pp. 2009-2017, September 2006.

[15] B. Linares-Barranco and T. Serrano-Gotarredona, "On the design and characterization of femtoampere current-mode circuits," *IEEE J. Solid-State Circuits*, vol. 38, no. 8, pp. 1353-1363, August 2003.

[16] P. E. Allen and D. R. Holberg, "CMOS analog circuit design," Oxford University Press, 2nd Edition, Chapter 5, pp. 184, FIG. 5.2-5, 2002.

[17] Y. Ni and M. Onabajo, "A low-power temperature-compensated CMOS relaxation oscillator," *Analog Integrated Circuits and Signal Processing*, vol. 79, no. 2, pp. 309-317, May 2014.

[18] L. Xu, J. Feng, Y. Ni, and M. Onabajo, "Test signal generation for the calibration of analog front-end circuits in biopotential measurement applications," in *Proc. IEEE Intl. Midwest Symp. on Circuits and Systems (MWSCAS)*, pp. 949-952, August 2014.

[19] M. Mano and C. Kime, "Sequential Circuits," in Logic and Computer Design Fundamentals, 1st ed., Upper Saddle River, Prentice Hall, 1997, ch. 4, pp. 190-191.

[20] N. H. E. Weste and D. M. Harris, "Array Subsystems," in CMOS VLSI Design a Circuits and Systems Perspective, 4th ed., Boston, Addison-Wesley, 2011, ch. 12, pp. 498-502.

[21] K. Wang, C.-H. Chang, and M. Onabajo, "A fully-differential CMOS low-pass notch filter for biosignal measurement devices with high interference rejection," in Proc. IEEE Intl. Midwest Symp. on Circuits and Systems (MWSCAS), pp. 1041-1044, August 2014.

What is claimed is:

1. An instrumentation amplifier device comprising:
an instrumentation amplifier comprising:
   a differential input stage comprising an inverting input terminal and a non-inverting input terminal;
   an output stage driven by the input stage;
   a direct current feedback loop from the output stage to the input stage; and
   a negative capacitance generation feedback circuit between the input stage and the direct current feedback loop, wherein a negative capacitance is generated at the input stage to cancel parasitic capacitances at the inverting input terminal and the non-inverting input terminal and thereby boost input impedance, wherein the negative capacitance generation feedback circuit comprises:
      a first negative impedance converter circuit connected in parallel between the inverting input terminal and a first internal node of the instrumentation amplifier; and
      a second negative impedance converter circuit connected in parallel between the non-inverting terminal and a second internal node of the instrumentation amplifier.

2. The instrumentation amplifier device of claim 1, wherein gains from the first and second internal nodes are out of phase.

3. The instrumentation amplifier device of claim 1, wherein each negative impedance converter circuit comprises a plurality of programmable capacitors disposed in parallel.

4. The instrumentation amplifier device of claim 3, wherein the instrumentation amplifier is calibratable by setting each programmable capacitor to be on or off to maximize the input impedance boosting.

5. The instrumentation amplifier device of claim 1, wherein the negative capacitance generation feedback circuit cancels at least in part input capacitance to the input stage generated by one or more of an electrode cable, a printed circuit board, and an integrated circuit package connected to the input stage.

6. The instrumentation amplifier device of claim 1, wherein the negative capacitance generation feedback circuit is operable to boost the input impedance to at least 100 MΩ, and the instrumentation amplifier is operable to measure input biosignals having frequencies of up to at least 50 Hz.

7. An instrumentation amplifier device, comprising:
an instrumentation amplifier comprising:
   a differential input stage comprising an inverting input terminal and a non-inverting input terminal;
   an output stage driven by the input stage;
   a direct current feedback loop from the output stage to the input stage;
   a negative capacitance generation feedback circuit between the input stage and the direct current feedback loop, and including programmable capacitors to generate the negative capacitance at the inverting input terminal and the non-inverting input terminal of the instrumentation amplifier; and
a calibration circuit comprising a processor operative in a calibration mode to:
   measure voltage at an output node of the instrumentation amplifier or of a subsequent gain or filtering stage;
   compare the measured voltage amplitude to a plurality of reference voltages;
   generate a respective plurality of control signals responsive to the comparison; and
   transmit the generated control signals to control the programmable capacitors of the instrumentation amplifier to optimize the negative capacitance generated at the input terminals of the instrumentation amplifier.

8. The instrumentation amplifier device of claim 7, wherein the calibration circuit includes:
   an analog-to-digital converter operative to provide the reference voltages, and
   a calibration unit comprising input ports to receive input signals from the analog to digital converter, a plurality of output ports to transmit control signals to switches at the programmable capacitors, and memory to store a code representative of a control signal to optimize the negative capacitance.

9. The instrumentation amplifier device of claim 7, wherein the calibration circuit includes a test current generator operative to inject a test current having a selected magnitude into the input of the instrumentation amplifier to generate a voltage at the output node.

10. A method of measuring biosignals comprising:
   receiving biosignals at an input stage of an instrumentation amplifier, the input stage including an inverting input terminal and a non-inverting input terminal;
   generating an amplified output signal at an output stage of the instrumentation amplifier;
   generating within the instrumentation amplifier a feedback loop from the output stage to the input stage; and
   boosting impedance at the input stage by generating a negative capacitance in the feedback loop from a first negative impedance converter circuit connected in parallel between the inverting input terminal and a first internal node of the instrumentation amplifier and a second negative impedance converter circuit connected in parallel between the non-inverting terminal and a second internal node of the instrumentation amplifier.

11. The method of claim 10, wherein the first and second internal nodes have out of phase gains.

12. A method of measuring biosignals comprising:
   receiving biosignals at an input stage of an instrumentation amplifier, the input stage including an inverting input terminal and a non-inverting input terminal;
   generating an amplified output signal at an output stage of the instrumentation amplifier;
   generating within the instrumentation amplifier a feedback loop from the output stage to the input stage;
   boosting impedance at the input stage by generating a negative capacitance in the feedback loop;
   connecting electrode cables to the input stage of the instrumentation amplifier; and
   calibrating the negative capacitance converter circuitry after connecting the electrode cables to maximize the boosting of the impedance at the input stage.

13. The method of claim 12, wherein the negative capacitance converter circuitry comprises a plurality of programmable capacitors, and the calibrating step comprises setting each of the programmable capacitors to on or off.

14. The method of claim 10, further comprising:
   connecting electrode cables to each of the inverting input terminal and the non-inverting input terminal, the electrode cables connected to dry electrodes; and
   receiving voltages representative of electroencephalography or electrocardiography signals.

15. The method of claim 10, further comprising boosting the impedance to at least 100 MΩ.

16. An instrumentation amplifier device comprising:
an instrumentation amplifier comprising
- a differential input stage comprising an inverting input terminal and a non-inverting input terminal;
- an output stage driven by the input stage;
- a direct current feedback loop from the output stage to the input stage; and
- a negative capacitance generation feedback circuit between the input stage and the direct current feedback loop, wherein a negative capacitance is generated at the input stage to cancel parasitic capacitances at the inverting input terminal and the non-inverting input terminal and thereby boost input impedance at the inverting input terminal and the non-inverting input terminal;

wherein the negative capacitance generation feedback circuit is connected in parallel between the input stage and internal nodes of the instrumentation amplifier, and gains from the internal nodes are out of phase, creating a differential-mode signal.

* * * * *